United States Patent
Daley et al.

(10) Patent No.: US 9,846,164 B2
(45) Date of Patent: *Dec. 19, 2017

(54) DETECTION OF HUMAN SOMATIC CELL REPROGRAMMING

(71) Applicant: Children's Medical Center Corporation, Boston, MA (US)

(72) Inventors: George Q. Daley, Weston, MA (US); In-Hyun Park, Boston, MA (US); Thorsten M. Schlaeger, Brookline, MA (US); Elayne Chan, Auburndale, MA (US); Sutheera Ratanasirintrawoot, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 95 days.

This patent is subject to a terminal disclaimer.

(21) Appl. No.: 14/194,586

(22) Filed: Feb. 28, 2014

(65) Prior Publication Data
US 2014/0336065 A1    Nov. 13, 2014

Related U.S. Application Data

(63) Continuation of application No. 13/120,192, filed as application No. PCT/US2009/057849 on Sep. 22, 2009, now Pat. No. 8,703,413.

(60) Provisional application No. 61/099,084, filed on Sep. 22, 2008.

(51) Int. Cl.
| | |
|---|---|
| *G01N 33/50* | (2006.01) |
| *G01N 33/53* | (2006.01) |
| *G01N 33/536* | (2006.01) |
| *G01N 33/58* | (2006.01) |
| *G01N 33/68* | (2006.01) |
| *G01N 33/569* | (2006.01) |
| *C12Q 1/68* | (2006.01) |
| *G01N 33/577* | (2006.01) |

(52) U.S. Cl.
CPC ....... *G01N 33/6872* (2013.01); *C12Q 1/6881* (2013.01); *G01N 33/5023* (2013.01); *G01N 33/5073* (2013.01); *G01N 33/56966* (2013.01); *C12Q 2600/124* (2013.01); *C12Q 2600/158* (2013.01); *G01N 33/502* (2013.01); *G01N 33/5044* (2013.01); *G01N 33/5047* (2013.01); *G01N 33/53* (2013.01); *G01N 33/536* (2013.01); *G01N 33/577* (2013.01); *G01N 33/58* (2013.01); *G01N 33/582* (2013.01); *G01N 33/6854* (2013.01); *G01N 2333/705* (2013.01); *G01N 2333/70596* (2013.01); *G01N 2333/90* (2013.01); *G01N 2500/10* (2013.01)

(58) Field of Classification Search
CPC ........... G01N 33/5073; G01N 33/6872; G01N 33/56966; G01N 2500/10; G01N 2333/70596; G01N 33/5023; G01N 33/5044; G01N 2333/78; G01N 2333/91011; G01N 2500/02; G01N 2500/04; G01N 2800/2835; G01N 2800/325; G01N 2800/52; G01N 33/5008; G01N 33/5011; G01N 33/5017; G01N 33/502; G01N 33/5026; G01N 33/5061; G01N 33/5082; G01N 33/542; G01N 33/6884; G01N 33/53; G01N 33/533; G01N 33/05
See application file for complete search history.

(56) References Cited

U.S. PATENT DOCUMENTS

| | | | |
|---|---|---|---|
| 8,703,413 | B2 | 4/2014 | Daley et al. |
| 2008/0274914 | A1 | 11/2008 | Yamanaka |
| 2009/0047263 | A1 | 2/2009 | Yamanaka et al. |
| 2009/0068742 | A1 | 3/2009 | Yamanaka |
| 2010/0041054 | A1 | 2/2010 | Mack |
| 2010/0062534 | A1 | 3/2010 | Hochedlinger et al. |
| 2011/0136145 | A1 | 6/2011 | Song et al. |
| 2012/0021519 | A1 | 1/2012 | Ichida et al. |

FOREIGN PATENT DOCUMENTS

| | | |
|---|---|---|
| WO | WO 2005/080598 A1 | 9/2005 |
| WO | WO 2007/069666 A1 | 6/2007 |

OTHER PUBLICATIONS

Apáti et al., High level functional expression of the ABCG2 multidrug transporter in undifferentiated human embryonic stem cells. Biochim Biophys Acta. Dec. 2008;1778(12):2700-9. doi: 10.1016/j.bbamem.2008.08.010. Epub Aug. 20, 2008.
Bhattacharya et al., Gene expression in human embryonic stem cell lines: unique molecular signature. Blood. Apr. 15, 2004;103(8):2956-64. Epub Dec. 30, 2003.
Brambrink et al., Sequential expression of pluripotency markers during direct reprogramming of mouse somatic cells. Cell Stem Cell. Feb. 7, 2008;2(2):151-9. doi: 10.1016/j.stem.2008.01.004.
Challen et al., A side order of stem cells: the SP phenotype. Stem Cells. Jan. 2006;24(1):3-12.
Chan et al., Live cell imaging distinguishes bona fide human iPS cells from partially reprogrammed cells. Nat Biotechnol. Nov. 2009;27(11):1033-7. doi: 10.1038/nbt.1580. Epub Oct. 11, 2009.
Daley et al., Broader implications of defining standards for the pluripotency of iPSCs. Cell Stem Cell. Mar. 6, 2009;4(3):200-1; author reply 202. doi: 10.1016/j.stem.2009.02.009.

(Continued)

Primary Examiner — Bridget E Bunner
(74) Attorney, Agent, or Firm — Wolf, Greenfield & Sacks, P.C.

(57) ABSTRACT

The methods and kits described herein are based, in part, to the discovery of a phenotype representing a fully-reprogrammed iPS cell and several reprogramming intermediates. The methods and kits described herein permit identification of fully-reprogrammed iPS cells and further permits one of skill in the art to monitor the emergence of iPS cells during the reprogramming process. The methods/kits can also be performed using real time using live cell imaging. Also described herein are methods for screening candidate reprogramming agents by monitoring the emergence of fully-reprogrammed iPS cells in the presence and absence of such an agent.

16 Claims, 16 Drawing Sheets

(56) References Cited

OTHER PUBLICATIONS

Dimos et al., Induced pluripotent stem cells generated from patients with ALS can be differentiated into motor neurons. Science. Aug. 29, 2008;321(5893):1218-21. doi: 10.1126/science.1158799. Epub Jul. 31, 2008.

Ellis et al., Alternative induced pluripotent stem cell characterization criteria for in vitro applications. Cell Stem Cell. Mar. 6, 2009;4(3):198-9; author reply 202. doi: 10.1016/j.stem.2009.02.010.

Hockemeyer et al., A drug-inducible system for direct reprogramming of human somatic cells to pluripotency. Cell Stem Cell. Sep. 11, 2008;3(3):346-53. doi: 10.1016/j.stem.2008.08.014.

Jaenisch et al., Stem cells, the molecular circuitry of pluripotency and nuclear reprogramming. Cell. Feb. 22, 2008;132(4):567-82. doi: 10.1016/j.cell.2008.01.015.

Lowry et al., Generation of human induced pluripotent stem cells from dermal fibroblasts. Proc Natl Acad Sci USA. Feb. 26, 2008;105(8):2883-8. doi: 10.1073/pnas.0711983105. Epub Feb. 15, 2008.

Maherali et al., A high-efficiency system for the generation and study of human induced pluripotent stem cells. Cell Stem Cell. Sep. 11, 2008;3(3):340-5. doi: 10.1016/j.stem.2008.08.003.

Maherali et al., Directly reprogrammed fibroblasts show global epigenetic remodeling and widespread tissue contribution. Cell Stem Cell. Jun. 7, 2007;1(1):55-70. doi: 10.1016/j.stem.2007.05.014.

Maherali et al., Guidelines and techniques for the generation of induced pluripotent stem cells. Cell Stem Cell. Dec. 4, 2008;3(6):595-605. doi: 10.1016/j.stem.2008.11.008.

Masaki et al., Heterogeneity of pluripotent marker gene expression in colonies generated in human iPS cell induction culture. Stem Cell Res. Nov. 2007;1(2):105-15. doi: 10.1016/j.scr.2008.01.001. Epub Jan. 31, 2008.

Okita et al., Generation of germline-competent induced pluripotent stem cells. Nature. Jul. 19, 2007;448(7151):313-7. Epub Jun. 6, 2007.

Okita et al., Generation of mouse induced pluripotent stem cells without viral vectors. Science. Nov. 7, 2008;322(5903):949-53. doi: 10.1126/science.1164270. Epub Oct. 9, 2008.

Park et al., Disease-specific induced pluripotent stem cells. Cell. Sep. 5, 2008;134(5):877-86. doi: 10.1016/j.cell.2008.07.041. Epub Aug. 7, 2008.

Park et al., Reprogramming of human somatic cells to pluripotency with defined factors. Nature. Jan. 10, 2008;451(7175):141-6. Epub Dec. 23, 2007.

Stadtfeld et al., Defining molecular cornerstones during fibroblast to iPS cell reprogramming in mouse. Cell Stem Cell. Mar. 6, 2008;2(3):230-40. doi: 10.1016/j.stem.2008.02.001. Epub Feb. 14, 2008.

Takahashi et al., Induction of pluripotent stem cells from adult human fibroblasts by defined factors. Cell. Nov. 30, 2007;131(5):861-72.

Takahashi et al., Induction of pluripotent stem cells from mouse embryonic and adult fibroblast cultures by defined factors. Cell. Aug. 25, 2006;126(4):663-76. Epub Aug. 10, 2006.

Wernig et al., In vitro reprogramming of fibroblasts into a pluripotent ES-cell-like state. Nature. Jul. 19, 2007;448(7151):318-24. Epub Jun. 6, 2007.

Yu et al., Induced pluripotent stem cell lines derived from human somatic cells. Science. Dec. 21, 2007;318(5858):1917-20. Epub Nov. 20, 2007.

Zhao et al., From fibroblasts to iPS cells: induced pluripotency by defined factors. J Cell Biochem. Nov. 1, 2008;105(4):949-55. doi: 10.1002/jcb.21871.

US 9,846,164 B2

DETECTION OF HUMAN SOMATIC CELL REPROGRAMMING

CROSS-REFERENCE TO RELATED APPLICATIONS

This application is a continuation of U.S. application Ser. No. 13/120,192, filed Jul. 11, 2011, which application is a national stage filing under 35 U.S.C §371 of International Application No. PCT/US2009/057849 filed Sep. 22, 2009, which was published under PCT Article 21(2) in English and which designates the U.S., and which claims the benefit under 35 U.S.C. §119(e) of the U.S. Provisional Application No. 61/099,084, filed on Sep. 22, 2008, the contents of all of which are incorporated herein by reference in their entirety.

This application claims benefit under 35 U.S.C. §119(e) of the U.S. Provisional Application No. 61/099,084, filed Sep. 22, 2008, the content of which is incorporated herein by reference in its entirety.

GOVERNMENT SUPPORT

This invention was made with government support under Grant No. DP1OD0002516 awarded by the National Institutes for Health (NIH). The government has certain rights in the invention.

FIELD OF THE INVENTION

The field of the invention relates to the identification of induced pluripotent stem cells.

BACKGROUND

Embryonic stem cells have properties of self-renewal and pluripotency that make them invaluable tools for studying tissue formation in vitro and a promising resource for regenerative medicine. Direct reprogramming of differentiated human cells into iPS cells provides a long-sought strategy to generate patient- and disease-specific pluripotent stem cells (Dimos, J. T., et al. (2008) *Science* 321, 1218-21; Park, I. H., et al. (2008) *Cell* 134, 877-86).

Identifying reprogrammed mouse fibroblasts and characterizing the kinetics of reprogramming is facilitated by molecular reporters integrated into the genomic loci of Fbx15, Oct4 and Nanog (Takahashi, K. & Yamanaka, S. (2006) *Cell* 126, 663-76; Okita, K., et al. (2007) *Nature* 448, 313-7; Wernig, M., et al. (2007) *Nature* 448, 318-24; Maherali, N., et al. (2007) *Cell Stem Cell* 1, 55-70), but there are no current methods to faithfully identify nascent human iPS cells amongst a large and heterogeneous population of fibroblasts and imperfectly reprogrammed cells. This has hindered efforts to define the molecular milestones, kinetics, and underlying mechanisms of reprogramming.

SUMMARY OF THE INVENTION

Described herein are methods for detecting and/or identifying reprogrammed cells (e.g., induced pluripotent stem cells) by detecting the presence of stem cell markers, or the absence/loss of expression of cell differentiation markers. The methods described herein relate to a combination of markers useful for identifying fully reprogrammed iPS cells, as well as assessing the stage of cells in the process of reprogramming. The methods described herein utilize the appearance of phenotypic markers of induced pluripotent stem cells or the disappearance of phenotypic markers of differentiated cells to identify or stage a reprogramming cell.

In one aspect, the methods described herein relate to a method for detecting somatic cell reprogramming, the method comprising: (a) contacting a somatic cell induced to reprogram or its progeny with a plurality of detectably labeled binding moieties that bind at least one of Rex1, DNMT3B, and/or ABCG2; and (b) detecting the binding of a plurality of the moieties to the at least one of Rex1, DNMT3B, and/or ABCG2 expressed by a cell in the culture; wherein binding indicates a reprogrammed cell.

Another aspect described herein relates to a method for identifying a fully reprogrammed iPS cell from a culture of cells, the method comprising: (a) contacting a somatic cell induced to reprogram or its progeny with a plurality of detectably labeled binding moieties that bind at least one of Rex1, DNMT3B, and/or ABCG2 expressed by a cell in the culture; and (b) detecting the binding of a plurality of the moieties to the cell or its progeny to the at least one of Rex1, DNMT3B, and/or ABCG2 expressed by a cell in the culture; wherein the presence of the at least one of Rex1, DNMT3B, and/or ABCG2 indicates a fully reprogrammed cell.

Described herein in another aspect is a method for screening for an agent that promotes reprogramming, the method comprising: (a) contacting a somatic cell with a plurality of detectably labeled moieties that bind at least one of Rex1, DNMT3B, and/or ABCG2 expressed by a cell in the culture, in the presence and absence of a candidate reprogramming agent; and (b) detecting the degree of cell labeling with the plurality of detectably labeled moieties to the at least one of Rex1, DNMT3B, and/or ABCG2; wherein if the level of expression of the at least one of Rex1, DNMT3B, and/or ABCG2 in the presence of the agent is higher compared to the level of the at least one of Rex1, DNMT3B, and/or ABCG2 in the absence of the agent, the agent enhances reprogramming.

In another aspect, described herein is a method for staging a reprogramming iPS cell, the method comprising (a) detecting expression of at least one of SSEA1, SSEA4, TRA160, CD9, DNMT3B, ABCG2, Fbx15, Ecat1, Esg1, Eras, Gdf3, Fgf4, Cripto, Dax 1, Zpf296, Slc2a3, Rex1, Utf1, Oct4, SOX2, Nat1 and/or NANOG in a somatic cell induced to reprogram, and detecting labeling with HOECHST dye of a cell in the culture at a plurality of time points; wherein detection of expression of at least one of SSEA1, SSEA4, TRA160, CD9, Fbx15, Ecat1, Esg1, Eras, Gdf3, Fgf4, Cripto, Dax1, Zpf296, Slc2a3, Rex1, Utf1, Oct4, SOX2, Nat1 and/or NANOG on the cell indicates an early stage of reprogramming of the cell; and wherein a HOECSHST$^{dim}$ phenotype of a cell expressing at least one of Rex1, DNMT3b, or ABCG2 correlates with a late stage of reprogramming of the cell.

In one embodiment of the above-described aspects, the method further comprises detecting a stem cell marker selected from the group consisting of SSEA1, SSEA4, TRA160, CD9, DNMT3B, ABCG2, Fbx15, Ecat1, Esg1, Eras, Gdf3, Fgf4, Cripto, Dax1, Zpf296, Slc2a3, Rex1, Utf1, Oct4, SOX2, Nat1 and/or NANOG.

In another embodiment of the aspects described above, the method further comprises detecting silencing of the expression of a viral reporter gene.

In another embodiment of the aspects described above, the somatic cell comprises a fibroblast.

In another embodiment of the aspects described above, expression of fibroblast marker CD13 is down-regulated.

In another embodiment of the aspects described above, the method further comprises repeating steps (b)-(c) at a plurality of time points.

In another embodiment of the aspects described above, each of the detectably labeled moieties comprises a fluorescent moiety.

In another embodiment of the aspects described above, the reprogrammed cell is pluripotent.

In another embodiment of the aspects described above, the reprogrammed cell comprises an SP phenotype.

In another embodiment of the aspects described above, the SP phenotype comprises a HOECHST$^{dim}$ phenotype.

In another embodiment of the aspects described above, the stem cell markers comprise TRA160, Rex1, DNMT3B, and/or ABCG2.

In another embodiment of the aspects described above, a cell in late stage reprogramming comprises a phenotype of DNMT3B+, Rex1+, CD13−, TRA160+, and HOECHST$^{dim}$.

Also described herein is a kit for identifying a fully-reprogrammed iPS cell, the kit comprising: (a) detectable binding moieties that selectively bind at least one of Rex1, DNMT3B, and/or ABCG2 and optionally comprising detectable moieties that selectively bind a stem cell marker selected from the group consisting of TRA160, Rex1, DNMT3B, ABCG2, SSEA4, or CD13; (b) packaging materials and instructions therefor.

Definitions

By "differentiated primary cell" or "somatic cell" is meant any cell that is not, in its native form, pluripotent as that term is defined herein. The term "somatic cell" also encompasses progenitor cells that are multipotent (e.g., produce more than one cell type) but not pluripotent (e.g., can produce cells from all three germ layers). It should be noted that placing many primary cells in culture can lead to some loss of fully differentiated characteristics. However, simply culturing such cells does not, on its own, render them pluripotent. The transition to pluripotency requires a re-programming stimulus beyond the stimuli that lead to partial loss of differentiated character in culture. Re-programmed pluripotent cells (also referred to herein as "induced pluripotent stem cells") are also characterized by the capacity for extended passaging without loss of growth potential, relative to primary cell parents, which generally have capacity for only a limited number of divisions in culture.

As used herein, the term "iPS cell" refers to a pluripotent stem cell artificially derived (e.g., induced) from a non-pluripotent cell, typically an adult somatic cell, for example, by inducing a forced expression of one or more genes.

As used herein the term "detecting somatic cell reprogramming" refers to detection of morphological or phenotypic changes that a cell undergoes during reprogramming. In particular, these changes can include the emergence of stem cell markers, or the downregulation of differentiation markers that occurs following induction of cell reprogramming. In general, "detecting somatic cell reprogramming" refers to the appearance or increase in expression of stem cell markers (e.g., SSEA1, SSEA4, TRA160, CD9, Fbx15, Ecat1, Esg1, Eras, Gdf3, Fgf4, Cripto, Dax1, Zpf296, Slc2a3, Rex1, Utf1, Oct4, SOX2, Nat1 and/or NANOG) and/or the disappearance or decrease in expression of differentiated cell markers.

By "increase in expression of stem cell markers" is meant an increase in expression of a stem cell marker of at least 10% in cells induced to reprogram compared to untreated cells; preferably "increase" refers to an increase in expression of at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 50-fold, at least 100-fold, at least 1000-fold or higher compared to the expression of a stem cell marker in somatic cells not induced to undergo reprogramming. The term "increase" encompasses, at a minimum, the detection of stem cell marker expression following induction of cellular reprogramming.

By "decrease in expression of differentiated cell markers" is meant a decrease in expression of differentiated cell markers (e.g., fibroblast marker CD13) of at least 10%, at least 20%, at least 30%, at least 40%, at least 50%, at least 60%, at least 70%, at least 80%, at least 90%, at least 95%, at least 99%, or even 100% (i.e., absent or below detection limits) compared to the expression of differentiated cell markers in somatic cells not induced to undergo reprogramming.

As used herein, the term "induced to reprogram" refers to any method useful for inducing somatic cells to reprogram to an induced pluripotent stem cell phenotype. In general somatic cells are induced to reprogram to iPS cells by viral delivery of nucleic acid sequences (e.g., Oct4, Sox2, Klf4, c-MYC etc.), however it is also contemplated herein that somatic cells are induced to reprogram by contacting a cell with a chemical or small molecule (e.g., Wnt pathway inhibitors; TGF-beta receptor antagonists) and/or placing the cell in specific culture conditions (e.g., hypoxia).

As used herein, the term "detectably labeled binding moieties" refers to a moiety capable of binding a stem cell marker (e.g., antibody, aptamer, small molecule, ligand etc.) and further comprises a detectable moiety such as e.g., a fluorescent moiety, a chemiluminescent moiety, colorimetric moiety etc.

As used herein, the phrase "silencing of the expression of a viral reporter gene" refers to a decrease in the expression of a viral reporter gene (assayed, for example, by detection of a fluorescent moiety on the viral reporter gene) of at least 20% in cells undergoing reprogramming compared to cells not induced to reprogram; preferably the decrease is at least 30%, at least 40%, at least 50%, at least 60%, at least 70%, at least 80%, at least 90%, at least 95%, at least 99%, or even 100% (i.e., no detectable expression of the viral reporter gene).

As used herein, the term "plurality of time points" refers to at least 2 or more time points (e.g., 3, 4, 5, 6, 7, 8, 9, 10, 11, 12, 13, 14, 15, 16, 17, 18, 18, 19, 20, 30, 40, 50, 60, 80, 100 time points or more). Similarly, the term "plurality of stem cell markers" refers to at least 2 or more stem cell markers (e.g., 3, 4, 5, 6, 7, 8, 9, 10, 11, 12, 13, 14, 15, 16, 17, 18, 18, 19, 20, 30, 40, 50, 60, 80, 100 stem cell markers or more)

As used herein, the term "SP phenotype" refers to a cell having a phenotype similar to a "side population" of stem cells based on the expression of HOESCHT, as described by e.g., Challen, S and M. Little *Stem Cells* (2006) 24(1):3-12.

The term "pluripotent" as used herein refers to a cell with the capacity, under different conditions, to differentiate to more than one differentiated cell type, and preferably to differentiate to cell types characteristic of all three germ layers. Pluripotent cells are characterized primarily by the ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers.

The term "re-programming" as used herein refers to the process of altering the differentiated state of a differentiated somatic cell to a pluripotent phenotype.

As used herein, the term "fully reprogrammed iPS cell" refers to an induced pluripotent stem cell characterized by a phenotype comprising at least one of DNMT3B+ and/or ABCG2+. This phenotype can further comprise the absence of expression of viral reporter genes as denoted herein by GFP$^{dim/-}$. Functionally, a "fully reprogrammed iPS cell" is defined as a pluripotent stem cell capable of differentiating into all three germ layers.

As used herein, the term "candidate reprogramming agent" refers to any agent that induces reprogramming of a somatic cell to an iPS cell phenotype and can include e.g., a small molecule, specific culture conditions, an antibody, an aptamer, a chemical, or a ligand etc.

As used herein the term "staging a reprogamming iPS cell" refers to the process of determining whether a reprogramming cell remains unprogrammed (e.g., no detectable stem cell marker expression), is in an early stage of reprogramming (e.g., expresses at least one stem cell marker and is HOESCHT$^{bright}$) or is in the late stages of reprogramming/fully reprogrammed (e.g., expresses at least one stem cell marker and is HOESCHT$^{dim}$).

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

DETAILED DESCRIPTION

Figure 1A:
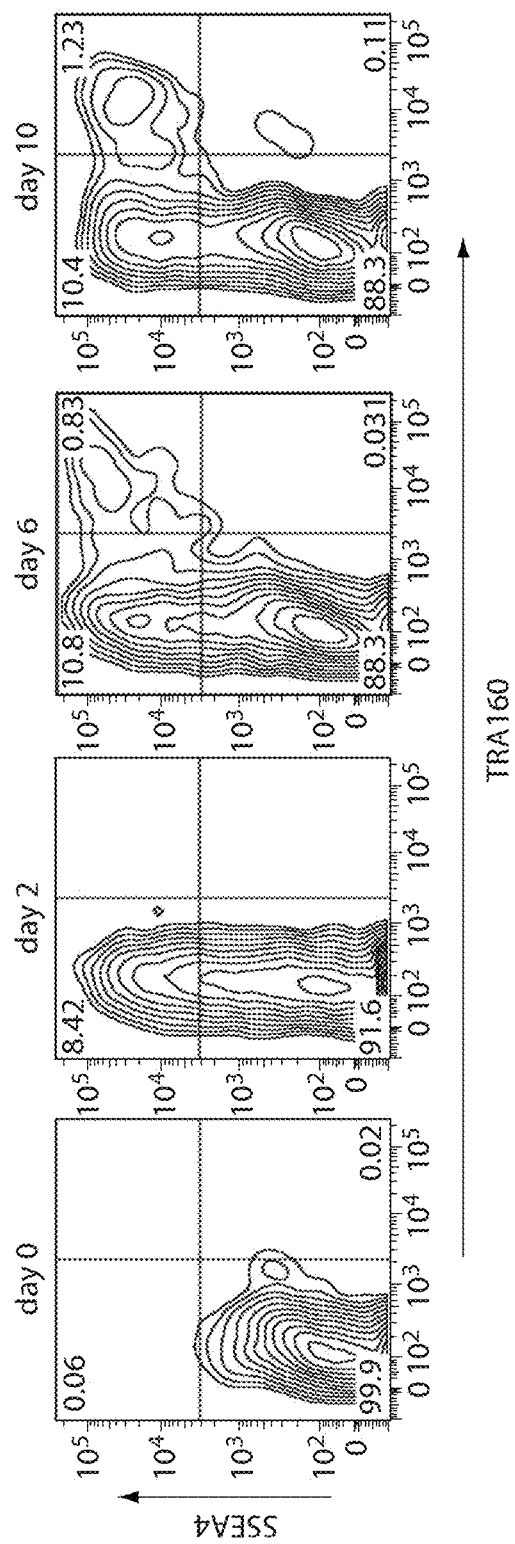
FIG. 1: FACS and Immunofluorescence time course analysis of human fibroblast reprogramming. (a) dH1f fibroblasts were analyzed by FACS for expression of pluripotency markers SSEA-4 and TRA-1-60 prior to transduction with reprogramming factor retroviruses (day 0), and at various time points post-transduction (day 2-10). (b) Summary of relative fluorescence intensities for TRA-1-60 (squares), SSEA-4 (triangles), Hoechst (circles), GFP (diamonds), and colony area (black) for emerging type III human iPS cell colonies. Dotted lines (before day 9) semi-quantitatively summarize changes based on FACS and imaging data. CD13 down- and SSEA-4 up-regulation begin around day 2 and are complete around day 6; proviral silencing becomes appreciable around day 4, and TRA-1-60 expression around day 6, with most cells remaining Hoechst$^{bright}$ until after day 9-11. Area, SSEA-4 and TRA-1-60 are arbitrarily set to 100% at day 21. Hoechst is set to 100% at day 9. GFP levels are relative to average GFP levels in non-silencing type I and II colonies for each timepoint. Scales are linear (Hoechst, GFP) and logarithmic (SSEA-4, TRA-1-60, area), respectively.

The methods described herein are based, in part, to the discovery of a phenotype representing a fully-reprogrammed iPS cell, as well as several reprogramming intermediates. The methods described herein permit identification of fully-reprogrammed iPS cells and further permits one of skill in the art to monitor the emergence of iPS cells during the reprogramming process. This method can also be performed in real time using live cell imaging. Also described herein are methods for screening candidate reprogramming agents by monitoring the emergence of fully-reprogrammed iPS cells in the presence and absence of such an agent.

Somatic Cells

While fibroblasts are generally used, essentially any primary somatic cell type can be substituted for a fibroblast with the methods described herein. Some non-limiting examples of primary cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. The cell can be a primary cell isolated from any somatic tissue including, but not limited to brain, liver, lung, gut, stomach, intestine, fat, muscle, uterus, skin, spleen, endocrine organ, bone, etc.

Where the cell is maintained under in vitro conditions, conventional tissue culture conditions and methods can be used, and are known to those of skill in the art. Isolation and culture methods for various cells are well within the abilities of one skilled in the art.

Further, the parental cell can be from any mammalian species, with non-limiting examples including a murine, bovine, simian, porcine, equine, ovine, or human cell. For clarity and simplicity, the description of the methods herein refers to fibroblasts as the parental cells, but it should be understood that all of the methods described herein can be readily applied to other primary parent cell types. In one embodiment, the somatic cell is derived from a human individual.

Reprogramming

The production of iPS cells is generally achieved by the introduction of nucleic acid sequences encoding stem cell-associated genes into a somatic cell. In general, these nucleic acids are introduced using retroviral vectors and expression of the gene products results in cells that are morphologically and biochemically similar to pluripotent stem cells (e.g., embryonic stem cells). This process of altering a cell phenotype from a somatic cell or progenitor cell phenotype to a stem cell-like phenotype is termed "reprogramming".

Reprogramming can be achieved by introducing a combination of stem cell-associated genes including, for example Oct3/4 (Pouf51), Sox1, Sox2, Sox3, Sox 15, Sox 18, NANOG, Klf1, Klf2, Klf4, Klf5, c-Myc, 1-Myc, n-Myc and LIN28. In general, successful reprogramming is accomplished by introducing Oct-3/4, a member of the Sox family, a member of the Klf family, and a member of the Myc family to a somatic or progenitor cell. In one embodiment of the methods described herein, reprogramming is achieved by delivery of Oct-4, Sox2, c-Myc, and Klf4 to a somatic cell (e.g., fibroblast). In one embodiment, the nucleic acid sequences of Oct-4, Sox2, c-MYC, and Klf4 are delivered using a viral vector, such as an adenoviral vector, a lentiviral vector or a retroviral vector.

While it is understood that reprogramming is usually accomplished by viral delivery of stem-cell associated genes, it is also contemplated herein that reprogramming can be induced using other delivery methods.

The efficiency of reprogramming (i.e., the number of reprogrammed cells) can be enhanced by the addition of various small molecules as shown by Shi, Y., et al (2008) Cell-Stem Cell 2:525-528, Huangfu, D., et al (2008) Nature Biotechnology 26(7):795-797, Marson, A., et al (2008) Cell-Stem Cell 3:132-135, which are incorporated herein by reference in their entirety. It is contemplated that the methods described herein can also be used in combination with a single small molecule (or a combination of small molecules) that enhances the efficiency of induced pluripotent stem cell production. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), trichostatin (TSA), and inhibitors of the TGF-β signaling pathway, among others. It is also contemplated herein that inhibitors can be used alone or in combination with other small molecule(s) to replace one or more of the reprogramming factors used for the production of iPS cells.

Cell Markers

In one embodiment, the emergence of an induced pluripotent stem cell is determined, in part, by the loss of expression of a cell marker for differentiated cell types. For example, a reprogrammed fibroblast loses expression of the fibroblast marker CD13. Distinct cell types are often characterized by a particular set of cell surface markers, which are known to those of skill in the art. Thus, a skilled artisan can identify a marker for the particular cell type of the artisan's choice and monitor the loss of expression of the marker during reprogramming to aid in the identification of an iPS cells using the methods described herein.

Stem cell markers are typically present on stem cells but are lost during cell differentiation. One of skill in the art can measure the emergence of a stem cell marker(s) known in the art with the methods described herein to identify reprogrammed iPS cells. Particularly preferred stem cell markers for use with the methods described herein include e.g., SSEA1, SSEA4, TRA160, CD9, DNMT3B, ABCG2, Fbx15, Ecat1, Esg1, Eras, Gdf3, Fgf4, Cripto, Dax1, Zpf296, Slc2a3, Rex1, Utf1, Oct4, SOX2, Nat1 and/or NANOG.

Teratoma Assay for Confirming Pluripotency

The pluripotent stem cell character of the isolated cells can be confirmed by any of a number of tests evaluating the expression of ES markers and the ability to differentiate to cells of each of the three germ layers. As one example, teratoma formation in nude mice can be used to evaluate the pluripotent character of the isolated clones. The cells are introduced to nude mice and histology is performed on a tumor arising from the cells. The growth of a tumor comprising cells from all three germ layers further indicates that the cells are pluripotent stem cells.

Detectable Binding Moieties

A detectable binding moiety, as that term is used herein, refers to an agent that can specifically bind a cell marker and further comprises a reporter moiety for detection of binding. Some non-limiting examples of detectable binding moieties include antibodies, aptamers, ligands, small molecules, and the like. In one embodiment, an antibody is used herein as a detectable binding moiety.

Antibodies that can be used according to the methods described herein include complete immunoglobulins, antigen binding fragments of immunoglobulins, as well as antigen binding proteins that comprise antigen binding domains of immunoglobulins. Antigen binding fragments of immunoglobulins include, for example, Fab, Fab', F(ab')2, scFv and dAbs. Modified antibody formats have been developed which retain binding specificity, but have other characteristics that may be desirable, including for example, bispecificity, multivalence (more than two binding sites), and compact size (e.g., binding domains alone).

Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Multiple single chain antibodies, each single chain having one VH and one VL domain covalently linked by a first peptide linker, can be covalently linked by at least one or more peptide linker to form multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of linker amino acid residues is approximately one hundred.

Two single chain antibodies can be combined to form a diabody, also known as a bivalent dimer. Diabodies have two chains and two binding sites, and can be monospecific or bispecific. Each chain of the diabody includes a VH domain connected to a VL domain. The domains are connected with linkers that are short enough to prevent pairing between domains on the same chain, thus driving the pairing between complementary domains on different chains to recreate the two antigen-binding sites.

Three single chain antibodies can be combined to form triabodies, also known as trivalent trimers. Triabodies are constructed with the amino acid terminus of a VL or VH domain directly fused to the carboxyl terminus of a VL or VH domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific.

Thus, antibodies useful in the methods described herein include, but are not limited to, naturally occurring antibodies, bivalent fragments such as (Fab')$_2$, monovalent fragments such as Fab, single chain antibodies, single chain Fv (scFv), single domain antibodies, multivalent single chain antibodies, diabodies, triabodies, and the like that bind specifically with an antigen (e.g., a TGFβR epitope).

Antibodies for use in the methods described herein can be obtained from commercial sources such as AbCam (Cambridge, Mass.), New England Biolabs (Ipswich, Mass.), Santa Cruz Biotechnologies (Santa Cruz, Calif.), Biovision (Mountain View, Calif.), R&D Systems (Minneapolis, Minn.), and Cell Signaling (Danvers, Mass.), among others. Antibodies can also be raised against a polypeptide or portion of a polypeptide by methods known to those skilled in the art. Antibodies are readily raised in animals such as rabbits or mice by immunization with the gene product, or a fragment thereof. Immunized mice are particularly useful for providing sources of B cells for the manufacture of hybridomas, which in turn are cultured to produce large quantities of monoclonal antibodies. Antibody manufacture methods are described in detail, for example, in Harlow et al., Eds., *Antibodies: A Laboratory Manual*, Cold Spring Harbor Laboratory, New York (1988), which is hereby incorporated by reference in its entirety.

While both polyclonal and monoclonal antibodies can be used in the methods described herein, it is preferred that a monoclonal antibody is used where conditions require increased specificity for a particular protein.

For measuring the amount of a molecule that is present, a convenient method is to label a binding moiety (e.g., an antibody) with a detectable moiety, which may be fluorescent, luminescent, radioactive, enzymatically active, etc., particularly a molecule specific for binding to the stem cell marker with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques.

Exemplary fluorescent moieties useful for labeling binding moieties include e.g., GFP, YFP, EGFP, EYFP EBFB, DsRed, RFP, and fluorescent variants thereof.

Live Imaging

In one embodiment, detection of reprogramming intermediate cells and/or emergence/identification of fully-reprogrammed iPS cells is performed in real time using live image techniques. In such techniques, the cells are not fixed and can be monitored over a series of time points if so desired by one of skill in the art.

Exemplary methods for live imaging of cells are known to those of skill in the art and/or are provided herein in the Examples section.

Candidate Reprogramming Agents

In one embodiment, the methods described herein are useful for screening candidate agents that effect reprogramming in cells. As used herein the term "agent" refers to any organic or inorganic molecule, including modified and unmodified nucleic acids such as antisense nucleic acids, RNA interference agents such as siRNA or shRNA, peptides, peptidomimetics, receptors, ligands, and antibodies.

Small Molecules

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Small molecule libraries can be obtained commercially and screened for reprogramming efficacy by one of skill in the art.

Antibodies

Antibody agents useful in effecting reprogramming can be obtained using the methods discussed above in the "Antibodies" section.

RNA Interference

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B., J. of Virology 76(18):9225 (2002)), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease may be of at least 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as a nucleic acid-comprising agent which functions to inhibit expression of a target gene, by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be encoded by plasmids, retroviruses, and lentiviruses and expressed from, for example, the pol III U6 promoter, or another promoter (see, e.g., Stewart, et al., RNA Apr; 9(4):493-501 (2003), incorporated by reference herein in its entirety).

The target gene or sequence of the RNA interfering agent may be a cellular gene or genomic sequence, e.g. the TGFβR sequence. An siRNA may be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical in sequence to its target.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al., Nature Biotechnology 6:635-637 (2003). In addition to expression profiling, one may also screen the potential target sequences for similar sequences in the sequence databases to identify potential sequences which may have off-target effects. For example, according to Jackson et al. (Id.) 15, or perhaps as few as 11 contiguous nucleotides, of sequence identity are sufficient to direct silencing of non-targeted transcripts. Therefore, one may initially screen the proposed siRNAs to avoid potential off-target silencing using sequence identity analysis by any known sequence comparison methods, such as BLAST.

siRNA molecules need not be limited to those molecules containing only RNA, but, for example, further encompasses chemically modified nucleotides and non-nucleotides that effect RNA interference, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group or a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated.

The most preferred siRNA modifications include 2'-deoxy-2'-fluorouridine or locked nucleic acid (LNA) nucleotides and RNA duplexes containing either phosphodiester or varying numbers of phosphorothioate linkages. Such modifications are known to one skilled in the art and are described, for example, in Braasch et al., Biochemistry 42: 7967-7975 (2003). Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

siRNAs useful for targeting TGFβR or ALK5 expression can be readily designed and tested. Chalk et al. (Nucl. Acids Res. 33: D131-D134 (2005)) describe a database of siRNA sequences and a predictor of siRNA sequences. Linked to the sequences in the database is information such as siRNA thermodynamic properties and the potential for sequence-specific off-target effects. The database and associated predictive tools enable the user to evaluate an siRNA's potential for inhibition and non-specific effects. The database is available at on the world wide web at siRNA.cgb.ki.se.

Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. Nature 411:494-498 (2001); Elbashir, S. M., et al., Genes & Development 15:188-200 (2001); Harborth, J. et al., J. Cell Science 114:4557-4565 (2001); Masters, J. R. et al., Proc. Natl. Acad. Sci., USA 98:8012-8017 (2001); and Tuschl, T. et al., Genes & Development 13:3191-3197 (1999)). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al., Genes Dev. 16:948-958 (2002); McManus, M. T. et al., RNA 8:842-850 (2002); Paul, C. P. et al., Nat. Biotechnol. 20:505-508 (2002); Miyagishi, M. et al., Nat. Biotechnol. 20:497-500 (2002); Sui, G. et al., Proc. Natl. Acad. Sci., USA 99:5515-5520 (2002); Brummelkamp, T. et al., Cancer Cell 2:243 (2002); Lee, N. S., et al., Nat. Biotechnol. 20:500-505 (2002); Yu, J. Y., et al., Proc. Natl. Acad. Sci., USA 99:6047-6052 (2002); Zeng, Y., et al., Mol. Cell. 9:1327-1333 (2002); Rubinson, D. A., et al., Nat. Genet. 33:401-406 (2003); Stewart, S. A., et al., RNA 9:493-501 (2003)).

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Examples

Somatic cells can be reprogrammed into induced pluripotent stem (iPS) cells by enforced expression of transcription factors. Using serial live imaging of human fibroblast undergoing reprogramming, distinct colony types were identified that morphologically resemble embryonic stem cells yet differ in molecular phenotype and differentiation potential. By using expression of pluripotency markers, methylation at the Oct4 and Nanog promoters, and differentiation into teratomas, it was determined that only one represents true iPS cells, while the others represent reprogramming intermediates. Proviral silencing and expression of TRA-1-60, DNMT3B, and REX1, can be used to distinguish the fully reprogrammed state, whereas Alkaline Phosphatase, SSEA-4, GFD-3, NANOG, and TERT are insufficient as markers. It is also shown herein that reprogramming using chemically defined medium favors formation of fully reprogrammed relative to partially reprogrammed colonies. These data define molecular markers of the fully reprogrammed state and highlights the need for rigorous characterization and standardization of putative iPS cells.

Identified herein is a phenotype of early colonies of iPS cells during human fibroblast reprogramming. It was found that emerging cells destined to become bona fide human iPS cell lines down-regulate the fibroblast marker CD13, up-regulate the pluripotency markers SSEA-4 and TRA-1-60, silence the transgenes, re-activate expression of endogenous NANOG, and transiently assume a "Hoechst$^{dim}$" phenotype. Analysis of multiple markers is essential to distinguish the fully reprogrammed state from partially reprogrammed intermediates.

Reprogramming of human ES cell-derived fibroblasts was initially studied, since like mouse embryo-derived fibroblasts (MEFs) these cells can be reprogrammed at a relatively high efficiency (Park, I. H., et al. (2008) Nature 451, 141-6; Maherali, N., et al. (2008) Cell Stem Cell 3, 340-5; Hockemeyer, D., (2008). Cell Stem Cell 3, 346-53). The fibroblast cell line dH1f has been derived through in vitro differentiation of the human ES cell line H1OGN (Park, I. H., et al. (2008) Nature 451, 141-6). By immunofluorescence and flow cytometry, it was confirmed that multiple fibroblast cell lines (dH1f, BJ1, Detroit-551, ADA) are homogeneously CD13$^+$D7FIB$^+$SSEA-4$^-$TRA-1-60$^-$, while human ES cells and iPS cells are CD13$^-$D7FIB$^-$SSEA-4$^+$TRA-1-60$^+$ (data not shown).

Four reprogramming factors (OCT4, SOX2, KLF4, c-MYC) were introduced into dH1fs using MSCV-based retroviruses (Park, I. H., et al. (2008) Nat Protoc 3, 1180-6). Each virus carried the GFP reporter gene, allowing us to monitor proviral silencing. Initial FACS analyses revealed that in ~10% of transduced (GFP$^+$) cells, SSEA-4 expression is detected as early as day 2, whereas TRA-1-60 is only detected in a small subset of SSEA-4$^+$ cells around day 6-10 (FIG. 1a). Concomitantly, CD13 is rapidly down-regulated in about ⅓ of GFP$^+$ cells by day 6 (data not shown). However, because FACS analysis disrupts individual colonies and therefore precludes precise lineage tracing, definitive conclusions could not be drawn about the ultimate fate of these cells by FACS analysis alone. Moreover, the low single cell plating efficiency of human pluripotent stem cells poses additional challenges to fate analysis by cell sorting. Serial live cell imaging of emerging colonies was therefore performed by staining in situ with antibodies against SSEA-4, TRA-1-60, CD13, and the permeable DNA dye Hoechst. In some cases, parallel wells were fixed to assess nuclear expression of endogenous NANOG. Every 2-3 days the same 4 cm$^2$ area of the well was scanned by automated fluorescence microscopy. Images were reviewed retrospectively for regions where colonies of bona fide human iPS cell lines had formed (see below). This analysis allowed the applicants to follow the fate and phenotype of emerging human iPS cell colonies, to trace their origin back to individual cell clusters that occupy as little as ⅟₃₀₀,₀₀₀ of the well area, and to compare faithfully reprogrammed with partially reprogrammed colonies.

Figure 3A:
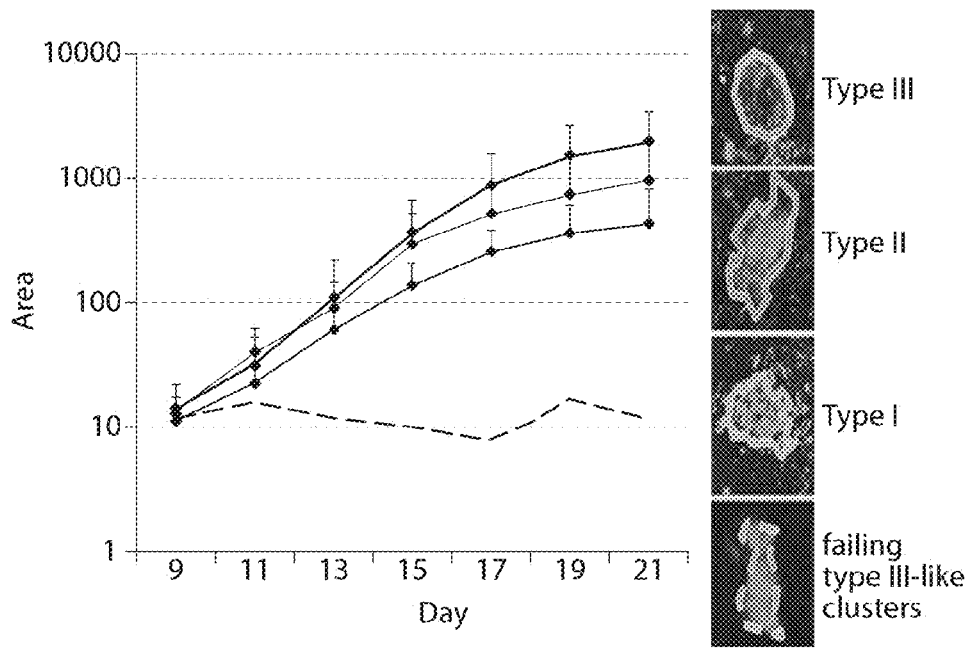
FIG. 3: Growth and potential of day 8 or 9 cell clusters. (a) The growth (area occupied) of cell clusters that give rise to type II-, or (bona fide iPS cells) colonies (see below). Clusters grow exponentially into colonies until further expansion slows down after day 15 in response to increasing overall cell and colony densities. Average size of Hoechst$^{bright}$ GFP$^{dim/-}$ SSEA-4$^+$ TRA-1-60$^+$ cell clusters that failed to expand is depicted by the discontinuous line. Area units are arbitrary, corresponding to approximate cell numbers of dense colonies (small clusters of cells and type I colonies tend to be less dense). (b) Comparison of the phenotype of TRA-1-60$^+$ day 8 cell clusters that go on to form bona fide iPS (type III) cell colonies to that of clusters that fail to grow into colonies. On average, iPS cell colony forming clusters contain more cells at day 8. Analysis was performed on cells that were not passaged after viral transduction.
Figure 3B:
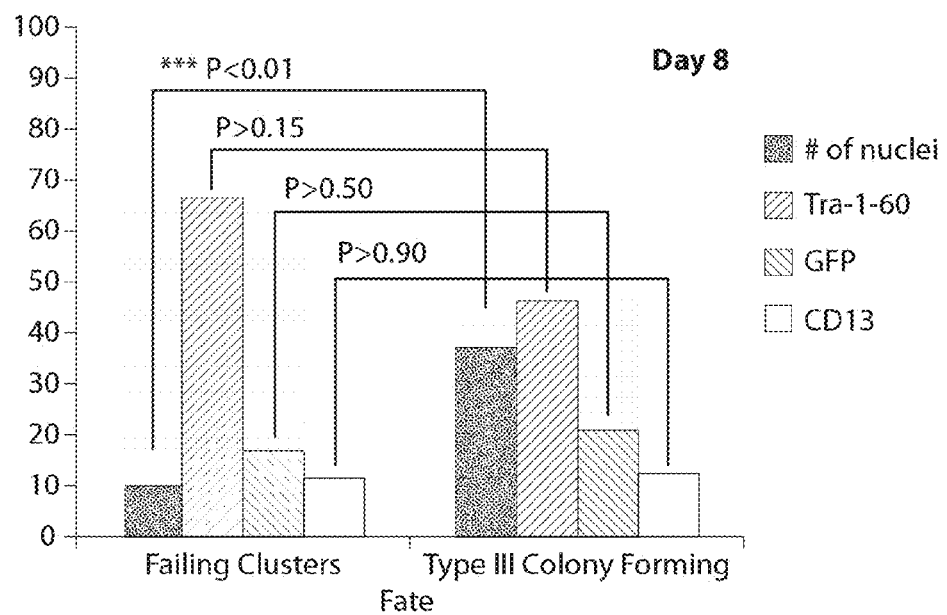

Emergence of rare human iPS cell (type III) colonies (GFP$^{dim/-}$CD13$^-$SSEA-4$^+$TRA-1-60$^+$) were observed on day 6-16 and days 9-15 (data not shown). Two other types of colonies also emerged: type II (GFP$^+$SSEA-4$^+$TRA-1-60$^-$) and type I (GFP$^+$SSEA-4$^-$TRA-1-60$^-$) (data not shown). iPS cell lines could only be established from colonies that developed from CD13$^-$GFP$^{dim/-}$SSEA-4$^+$TRA-1-60$^+$ cell clusters. Expression of NANOG correlated well with that of TRA-1-60: nuclear staining was first detectable in TRA-1-60$^+$ cell clusters around day 6 to 10 (data not shown), and all tested CD13$^-$GFP$^{dim/-}$TRA-1-60$^+$ colonies homogeneously expressed NANOG at day 16 (data not shown). In contrast, TRA-1-60$^+$ clusters that were SSEA-4$^-$ or remained GFP$^+$ failed to grow or give rise to proper iPS cell lines. Even among cell clusters that were TRA-1-60$^+$SSEA-4$^+$GFP$^{dim/-}$ at day 9 (i.e., that are otherwise indistinguishable from iPS cell colony forming cell clusters), the majority (70.5±6.6%) failed to grow (FIG. 3). The only feature of day 8 TRA-1-60$^+$ cell clusters that correlated with fate (failure to thrive vs. formation of iPS cell like colonies) was cellularity (~10 vs.>35 cells per cluster; see FIG. 3b). These observations highlight the stochastic nature of reprogramming and suggest that senescence or a low proliferative capacity limit reprogramming efficiencies.

Figure 1B:
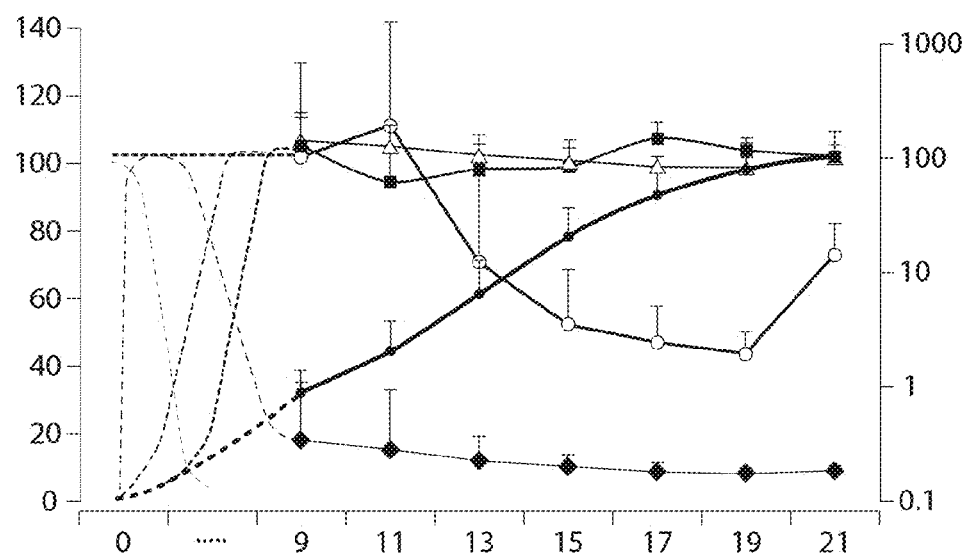
Figure 4A:
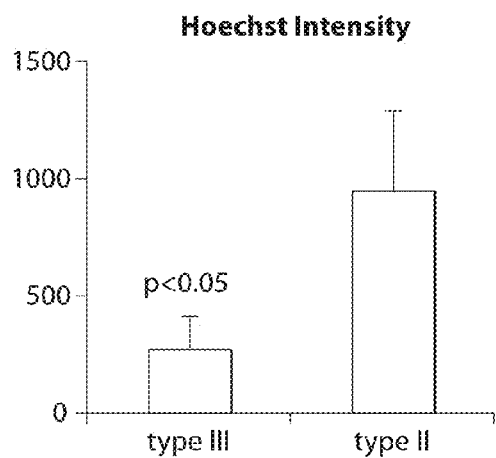
FIG. 4: Quantification of Hoechst staining intensities (average of colonies from the same well, Student's t-test; a). Type III colony Hoechst staining intensities increased upon cell fixation and re-staining with Hoechst, indicating an intact cell membrane is required for this phenotype (colony staining intensity normalized to neighboring fibroblast nuclear staining intensity before and after fixation, Student's t-test; b). Staining artifacts could be excluded since Hoechst$^{dim}$ and Hoechst$^{bright}$ colonies were often in direct contact (c; clockwise from upper-left: Hoechst, GFP, TRA-1-60, SSEA-4).
Figure 4B:
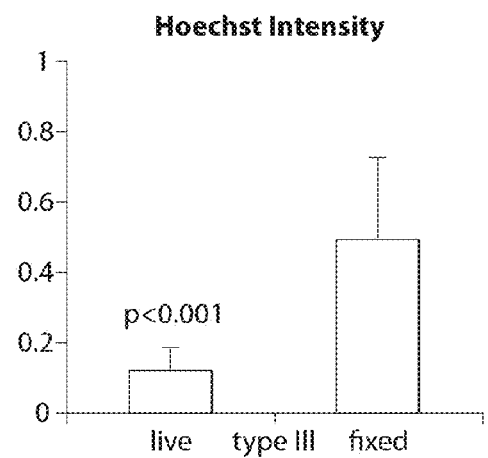
Figure 4C:
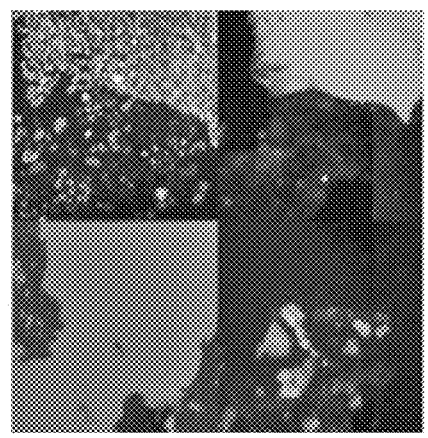

A change in the intensity of Hoechst staining was observed that was specific to clusters and colonies undergoing successful reprogramming (FIG. 4). While initially all cells are Hoechst$^{bright}$, emerging iPS cell colonies become Hoechst$^{dim}$ around day 10-13. FIG. 1b summarizes the changes observed in emerging iPS cell clusters and colonies. Of note, the growth phase begins at or before day 9, prior to acquisition of the Hoechst$^{dim}$ phenotype, and thus before reprogramming is complete.

In contrast to the rare cell clusters that become bona fide iPS cell colonies, the vast majority of fibroblasts infected with reprogramming factors fail to complete reprogramming. Some CD13$^+$GFP$^+$ cells formed large, early-emerging colonies of disperse, fibroblast-like cells that were generally SSEA-4$^-$ and expressed varying levels of CD13. These colonies, presumably related to previously described OCT4/MYC colonies, (Lowry, W. E., et al. (2008) Proc Natl Acad Sci USA 105, 2883-8) could clearly be distinguished by morphology alone from true iPS cell colonies. In contrast, colonies that appeared morphologically similar to human ES cells by phase contrast microscopy (i.e., small, tightly packed cells, with tight colony borders) segregated into three types. Relative to type II and type I colonies, maturing type III colonies appeared to stain less intensely with the cell permeable DNA dye Iloescht (data not shown). Colonies of tightly packed Hoechst$^{bright}$ GFP$^+$SSEA-4$^-$TRA-1-60$^-$ cells were labeled type I (data not shown). SSEA-4$^+$GFP$^+$TRA-1-60$^-$ colonies that remained Hoechst$^{bright}$ throughout the time course were labeled type II (data not shown). The colonies that proved to be bona fide iPS cells (CD13$^-$SSEA-4$^+$TRA-1-60$^+$GFP$^{dim/-}$NANOG$^+$) were labeled type III (data not shown).

Figure 2A:
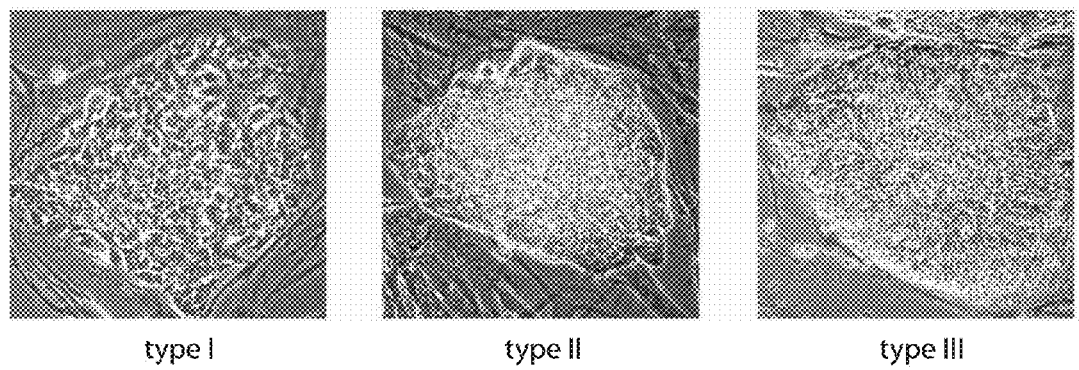
FIG. 2. Characterization of types I, II, and III colonies.
(a) Morphology of type-I, -II, and -III colonies under phase contrast microscopy. Three individual colonies from various type I, II, and III lines are shown (20× Phase; mouse fibroblast co-culture with KOSR/FGF-2 human ES cell media). All types of lines included colonies of densely packed cells, and type II and III colonies could be difficult to distinguish without live fluorescence imaging, especially at lower magnification or to an inexperienced observer. (b) Expression of OCT4, SOX2, KLF4, c-MYC, NANOG, GDF3, hTERT and REX1 were analyzed by quantitative real-time PCR in human ES (H1OGN, BGO1), types I (B7), II (F5, G2), III (9), and parental fibroblast (dH1f) cell lines. Samples were normalized against the internal control (β-actin) and plotted (log 10 scale) relative to the expression level in the human ES cell line H1OGN (leftmost column) which is arbitrarily set to 1. Black and grey bars represent total (endogenous and exogenous) and endogenous gene levels respectively. (c) Real-time PCR analysis of chromatin immunoprecipitation using antibodies against tri-methylated histone H3K4 and H3K27. Extracts were derived from parental fibroblast (dH1f), type I (B7), type II (C2, F5, G2), and type III (8, 9) cells. Shown are the fold enrichment of the reported 'bivalent' loci in human ES cells. Fold enrichment is the relative abundance of DNA fragments at the amplified region.

Heatmap representation of the marker staining intensities over time (days 9 to 21) demonstrated that the transient Hoechst$^{dim}$ phenotype of type III colonies correlates with the degree of silencing of retroviral GFP expression (data not shown). Without wishing to be bound by theory, the increase in the Hoechst signal of mature type III colonies may in part be due to elevated cellular densities and accumulation of dead/differentiated cells. However, human pluripotent stem cell lines are known to contain ABCG2-positive Hoechst$^{dim}$ cells (Apati, A., et al. (2008) Biochim Biophys Acta 1778, 2700-9). Type I and II colonies, in contrast, appear to be "frozen" in states that resemble intermediate stages of reprogramming. Individual colonies of types I, II and III were picked and cultured under human ES cell growth conditions. Some type I and most type II expansion cultures included tightly packed colonies that under phase contrast microscopy were reminiscent of human ES cell/iPS cell colonies (FIG. 2a). A number of each type were chosen for further characterization and were confirmed to have a normal karyotype. Immunostaining demonstrated that these lines generally maintained the same marker phenotype as the colonies they were derived from, and PCR analysis confirmed the presence of all four retroviral reprogramming factors in each line (data not shown).

Figure 2B:
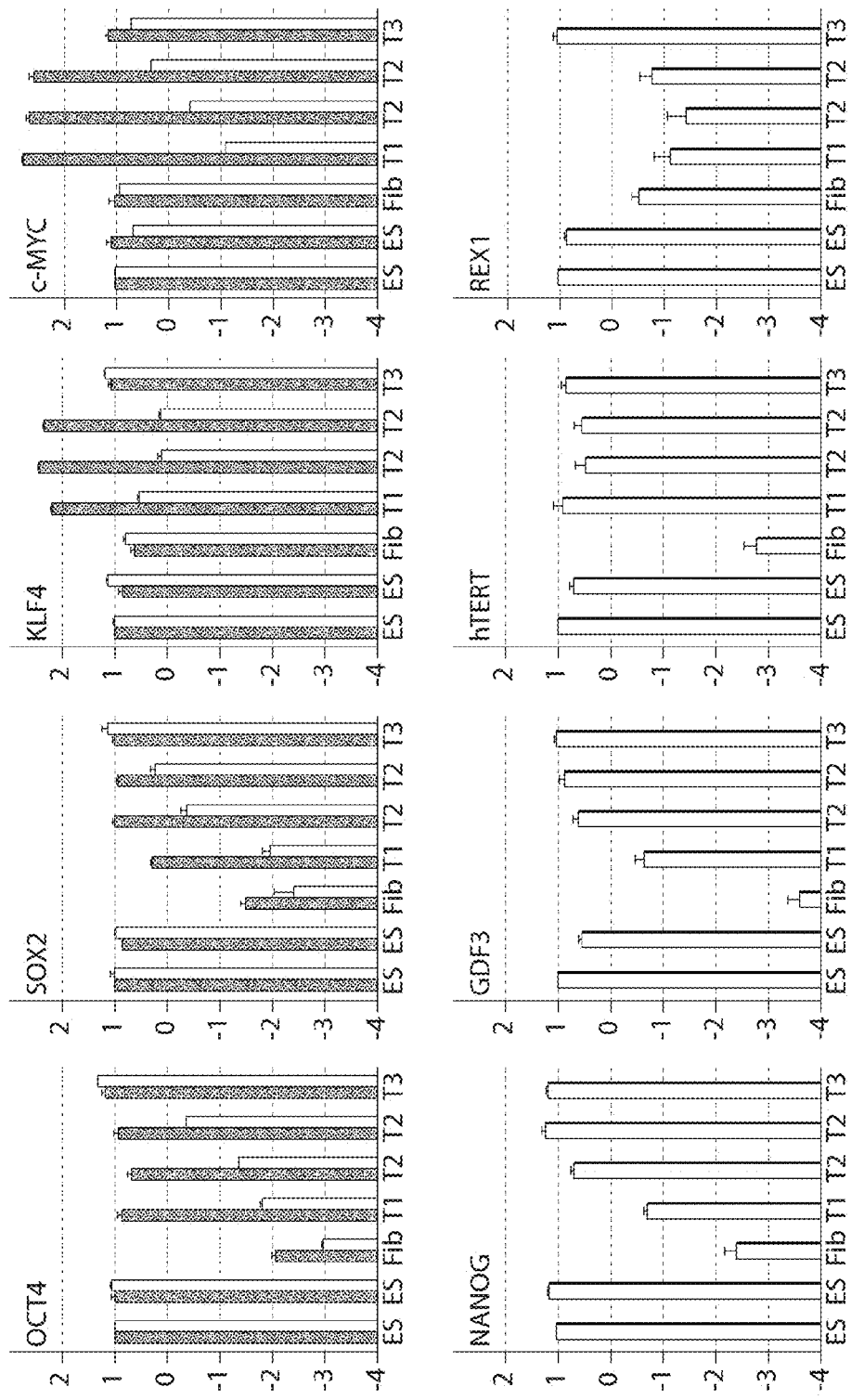
Figure 2C:
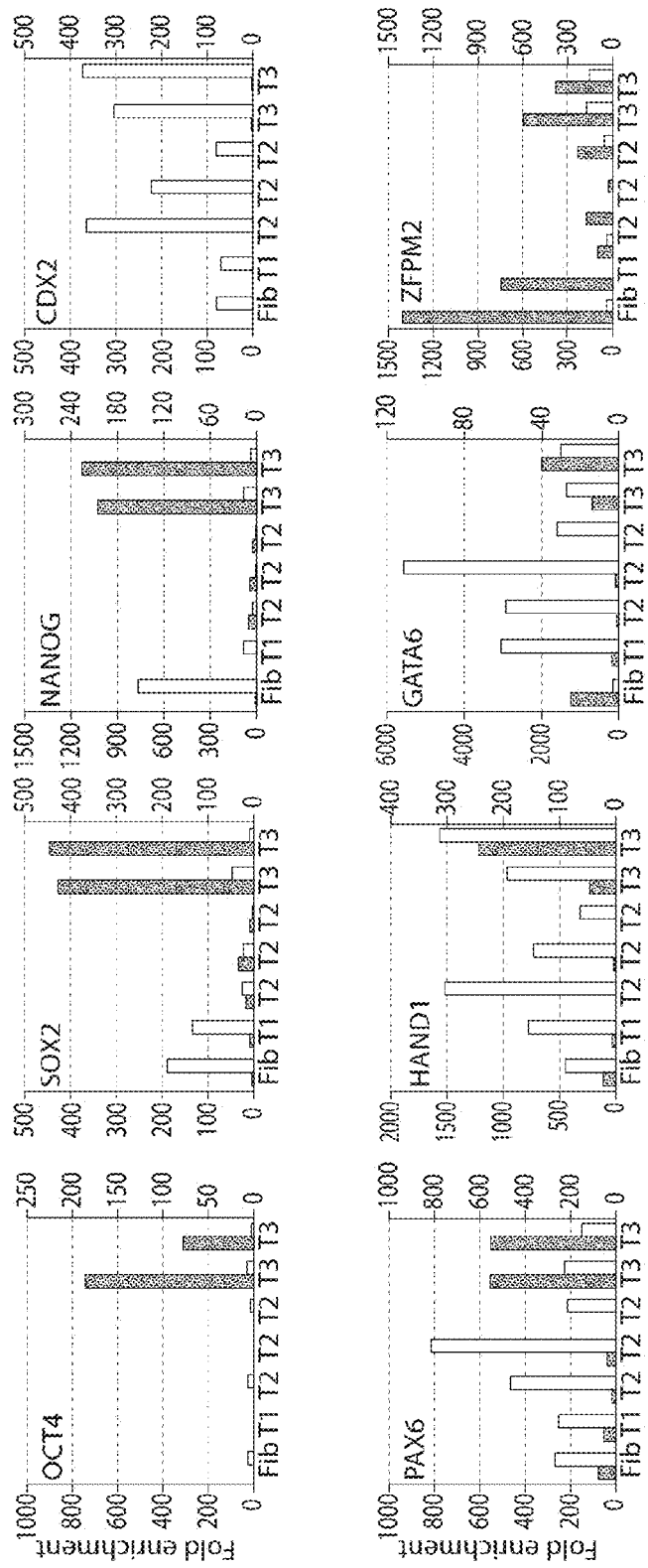
Figure 5:
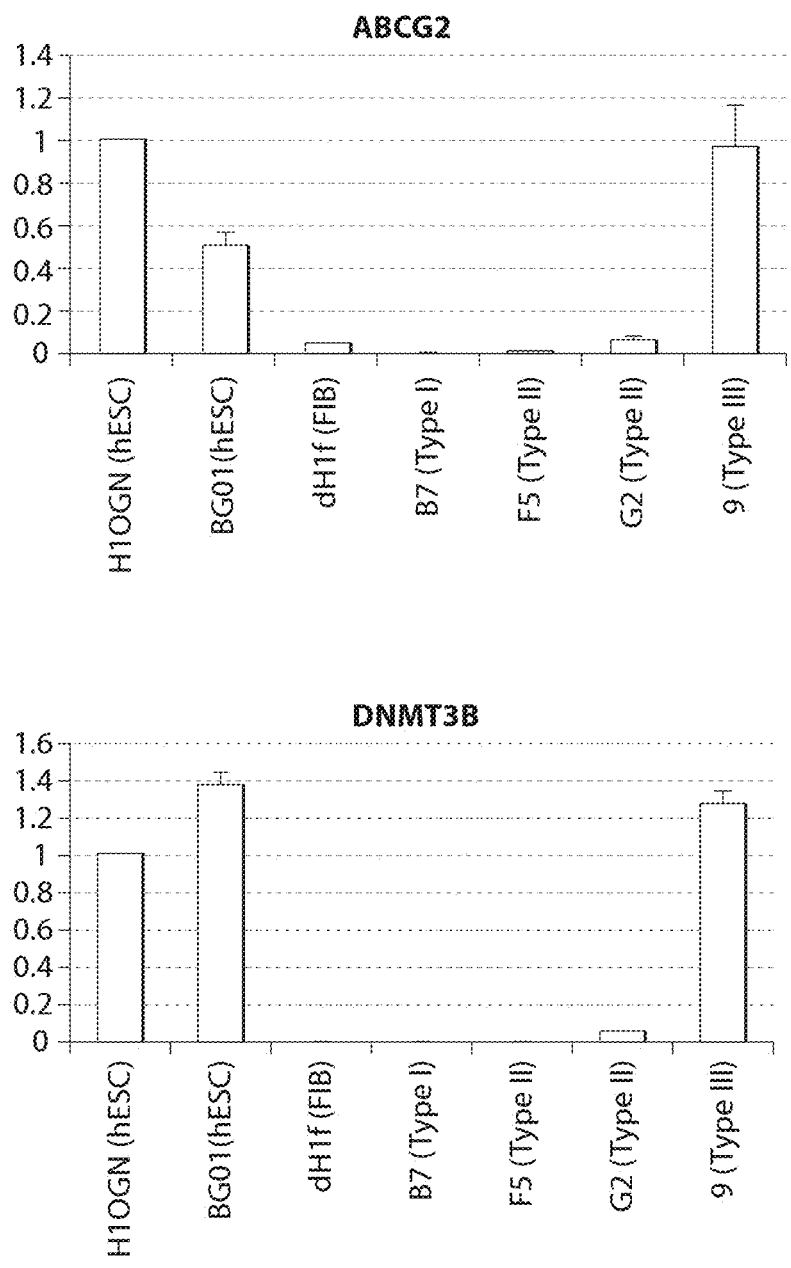
FIG. 5: Expression of ABCG2 and DNMT3B was analyzed by quantitative real-time PCR in human ES (H1OGN, BGO1), parental fibroblast (dH1f) cell lines, types I (B7), II (G2, F5) and III (9). Samples were normalized against the internal control (β-actin) and plotted relative to the expression level in the human ES cell line H1OGN (leftmost column).
Figure 6:
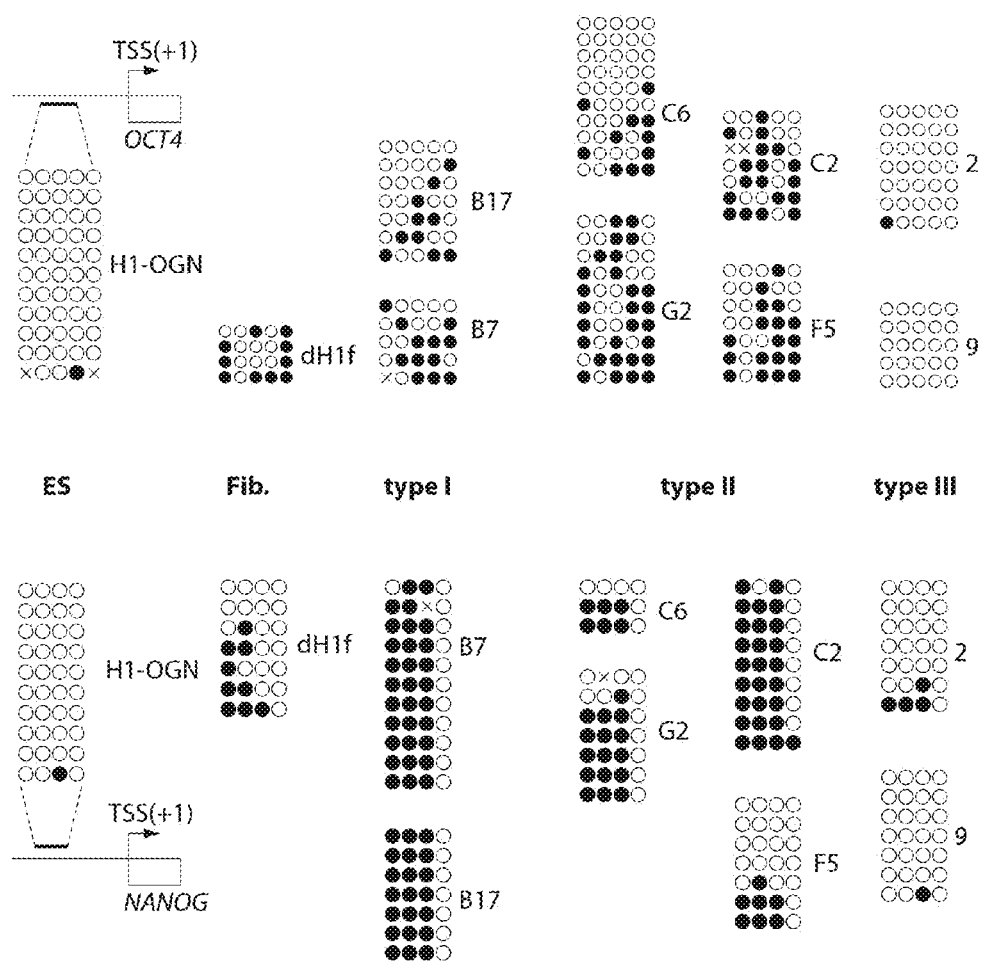
FIG. 6: Types I and II clones are methylated at the OCT4 and NANOG promoters similar to their fibroblast parent lines. Bisulfite sequencing analysis of the OCT4 and NANOG promoters in types I (B7, B17), II (C6, G2, C2, F5), and III (2, 9) clones. Shown also are the parental human ES cell (H1OGN)-derived fibroblast cell line, dH1f, and the human ES cell line H1OGN. Each horizontal row represents an individual sequencing reaction for a given amplicon. White circles represent unmethylated CpG dinucleotides; black circles represent methylated CpG dinucleotides.

Analysis of the gene expression and epigenetic state of these lines revealed a varying degree of reprogramming indicating that lines derived from type III colonies represent bona fide iPS cells whereas lines derived from type II and type I colonies are incompletely reprogrammed. Nuclear NANOG staining was undetectable in type I colonies, detectable in some type II cells, and homogeneously present in all type III colonies (data not shown). Similarly, multiple endogenous pluripotency mRNAs (OCT4, SOX2, NANOG and GDF3) showed a gradation of expression in type I, II, and III cell lines (FIG. 2b). hTERT expression was high in all types whereas REX1, DNMT3B and ABCG2 was selectively expressed in cultures of type III cells (FIG. 2b and FIG. 5). Hypomethylation of the NANOG and OCT4 gene promoters (FIG. 6), and histone modifications characteristic of the pluripotent state, including bivalency of developmental regulators as well as activation marks on OCT4, SOX2, and NANOG were also specific to type III and human ES cell cultures (FIG. 2c).

Figure 7A:
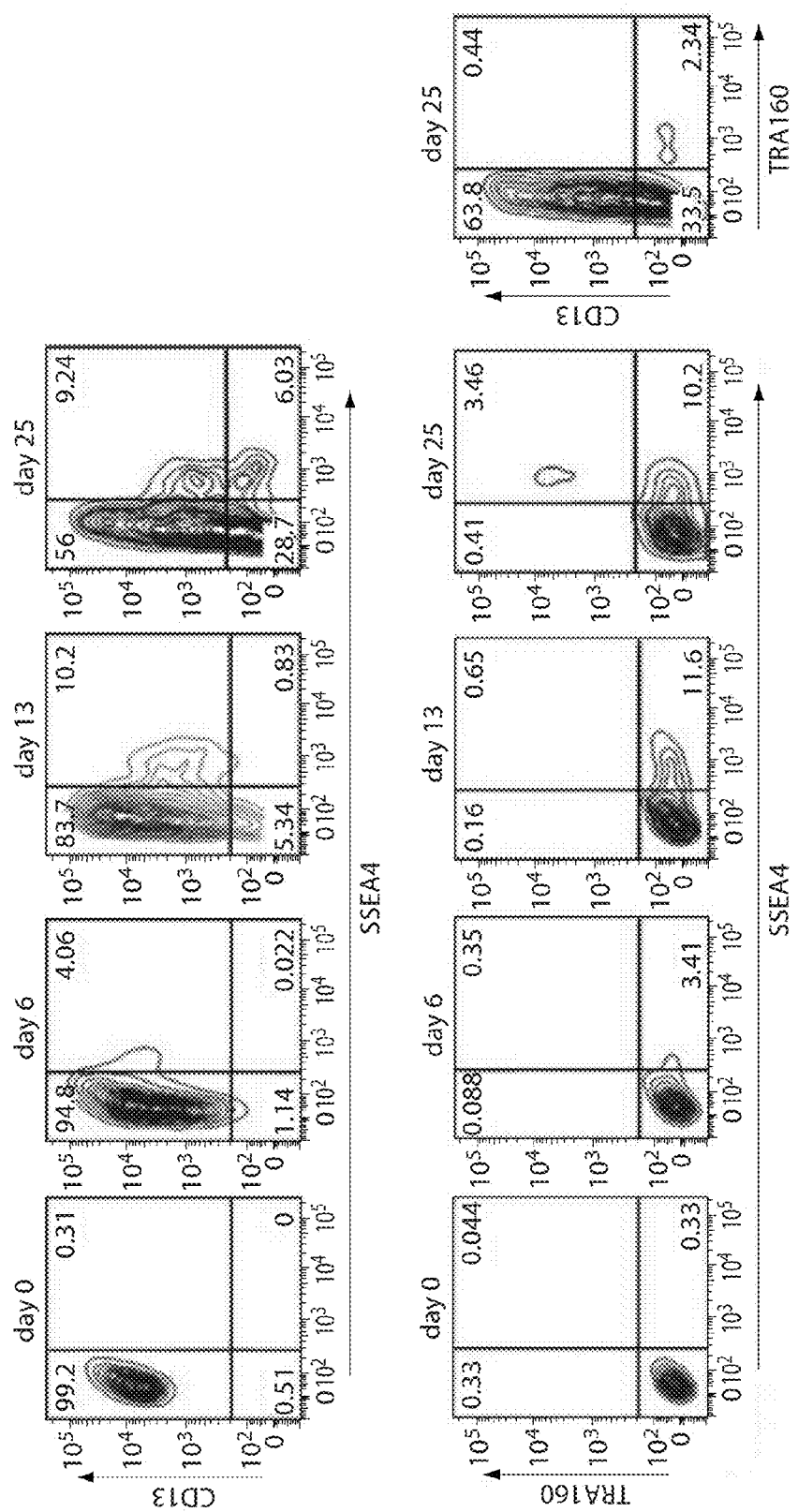
FIG. 7: FACS and Immunofluorescence time course analysis of BJ1 human primary fibroblast reprogramming. BJ1 fibroblast reprogramming cultures were analyzed by (a) FACS for expression of pluripotency markers SSEA-4 and TRA-1-60 and the fibroblast marker CD13 prior to transduction with reprogramming factor retroviruses (day 0), and at various time points post-transduction (day 6-25); (b) Three individual colonies from various type I, II, and III lines are shown (20× Phase; mouse fibroblast co-culture with KOSR/FGF-2 human ES cell media).
Figure 7B:
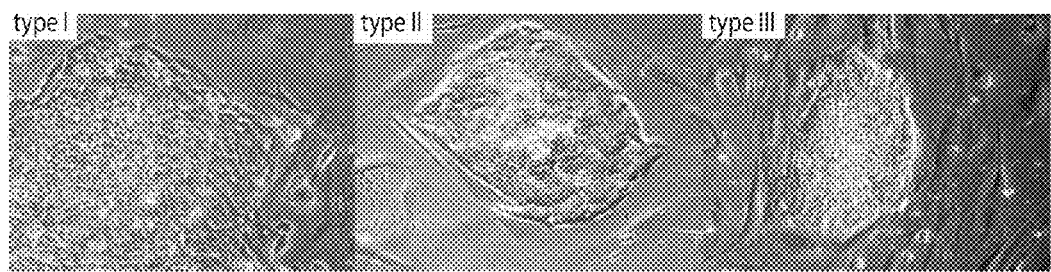
Figure 8A:
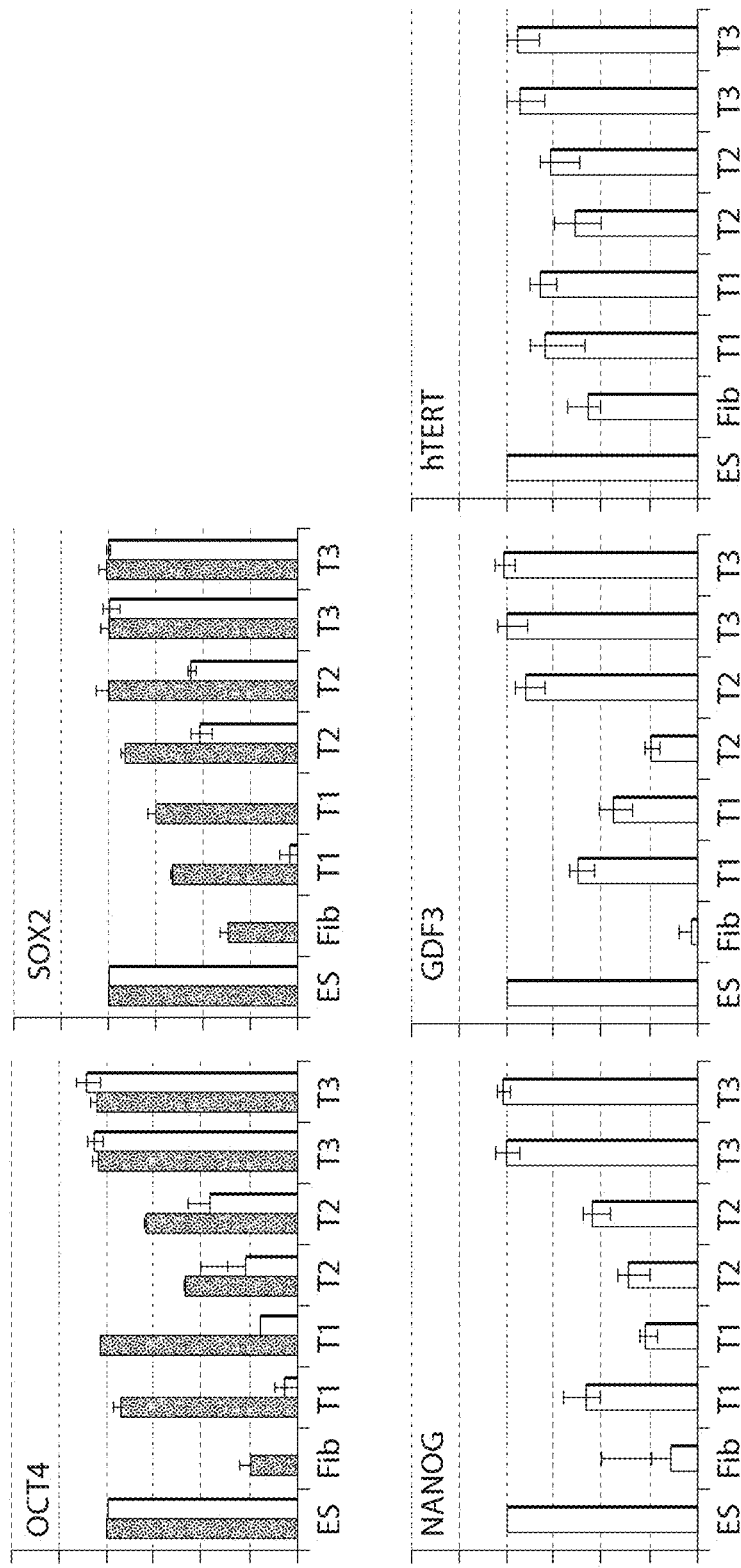
FIG. 8: Quantitative real time PCR and promoter methylation analysis of type I, II, III cell lines derived from BJ1 fibroblasts. (a) Expression of OCT4, SOX2, NANOG, GDF3 and hTERT were analyzed by quantitative real-time PCR in human ES (H1OGN), types I (11.3, 11.4), II (I.B, I.D), III (iPS 1, iPS 2), and parental fibroblast (BJ1) cell lines. Samples were normalized against the internal control (β-actin) and plotted (log 10 scale) relative to the expression level in the human ES cell line H1OGN (leftmost column) which is arbitrarily set to 1. Black and grey bars represent total (endogenous and exogenous) and endogenous gene levels respectively. (b) Expression of REX1, DNMT3B and ABCG2 were analyzed by quantitative real-time PCR. Samples were normalized against the internal control (β-actin) and plotted relative to the expression level in the human ES cell line H1OGN (leftmost column). (c) Bisulfite sequencing analysis of the OCT4 and NANOG promoters in types 1 (II.3, II.4), II (I.D), and III (iPS 1, IPS 5) clones. Shown also are the parental BJ1 fibroblast cell line and the human ES cell line H1OGN. Each horizontal row represents an individual sequencing reaction for a given amplicon. White circles represent unmethylated CpG dinucleotides; black circles represent methylated CpG dinucleotides.
Figure 8B:
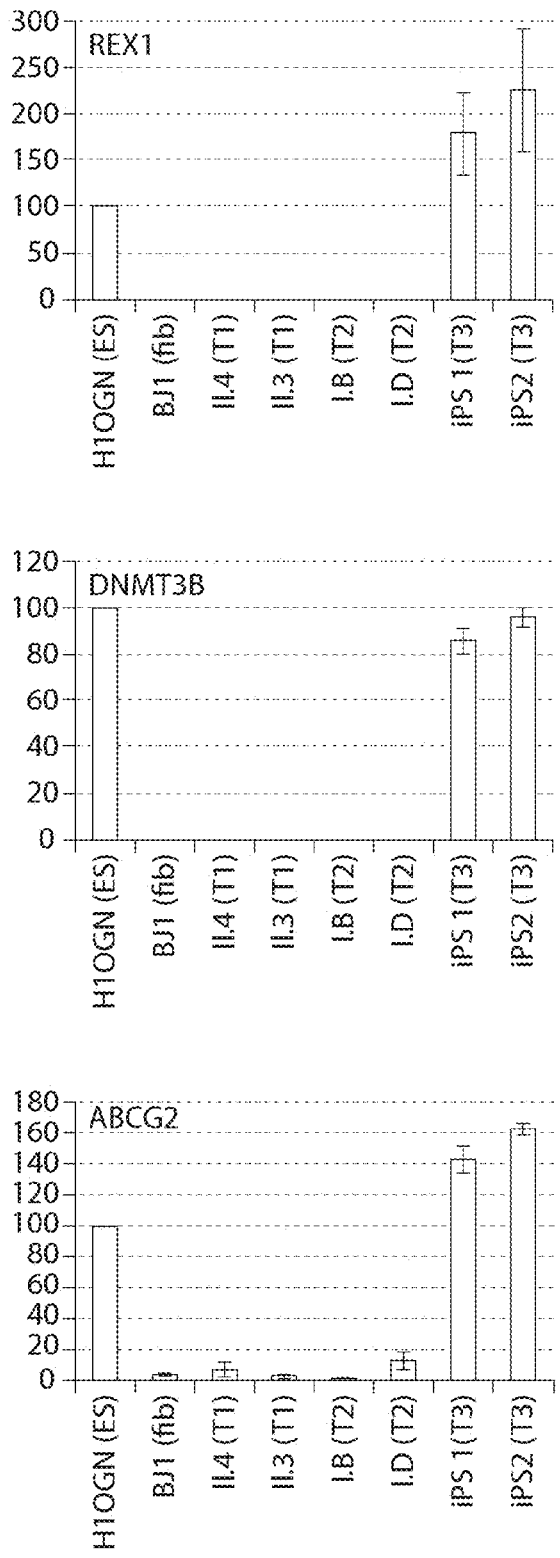
Figure 8C:
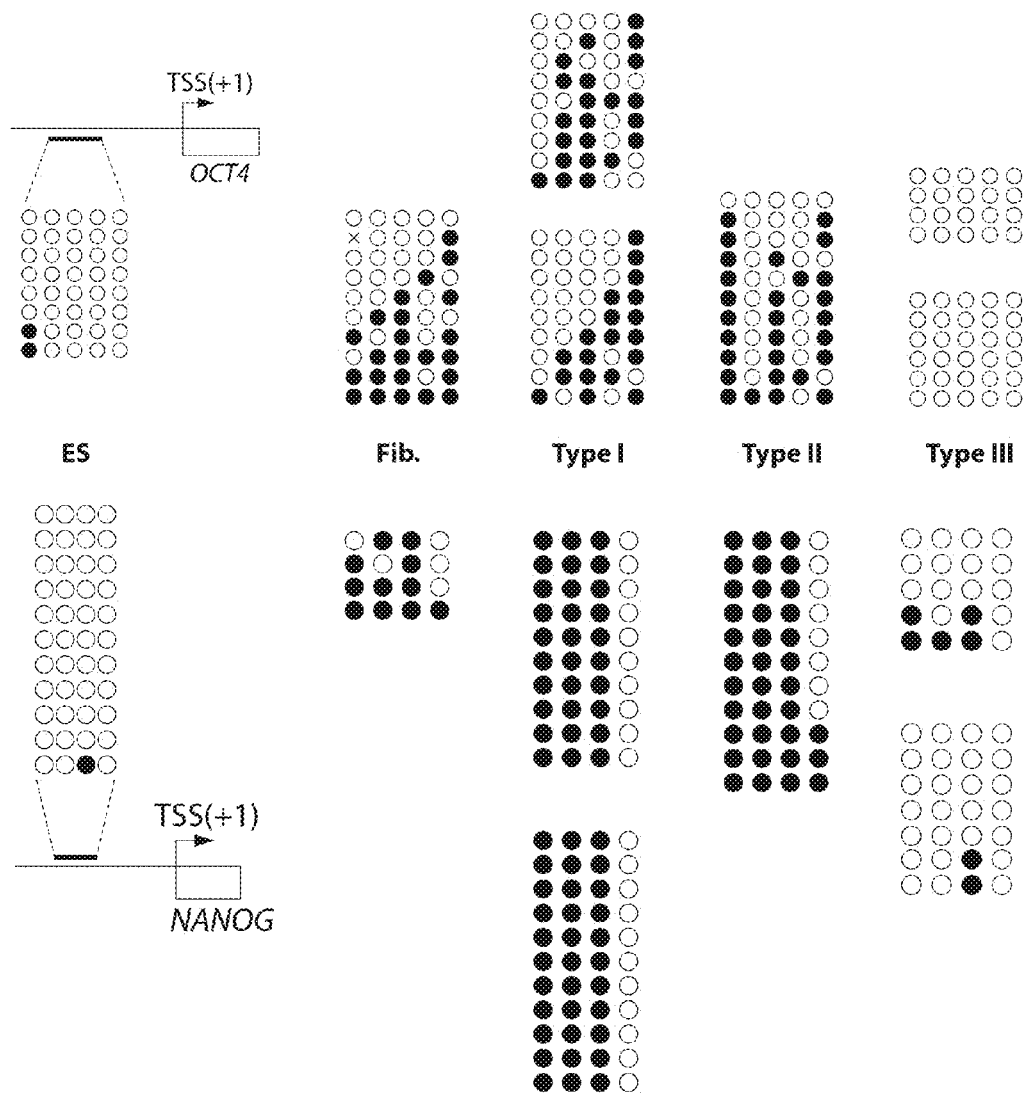
Figure 10:
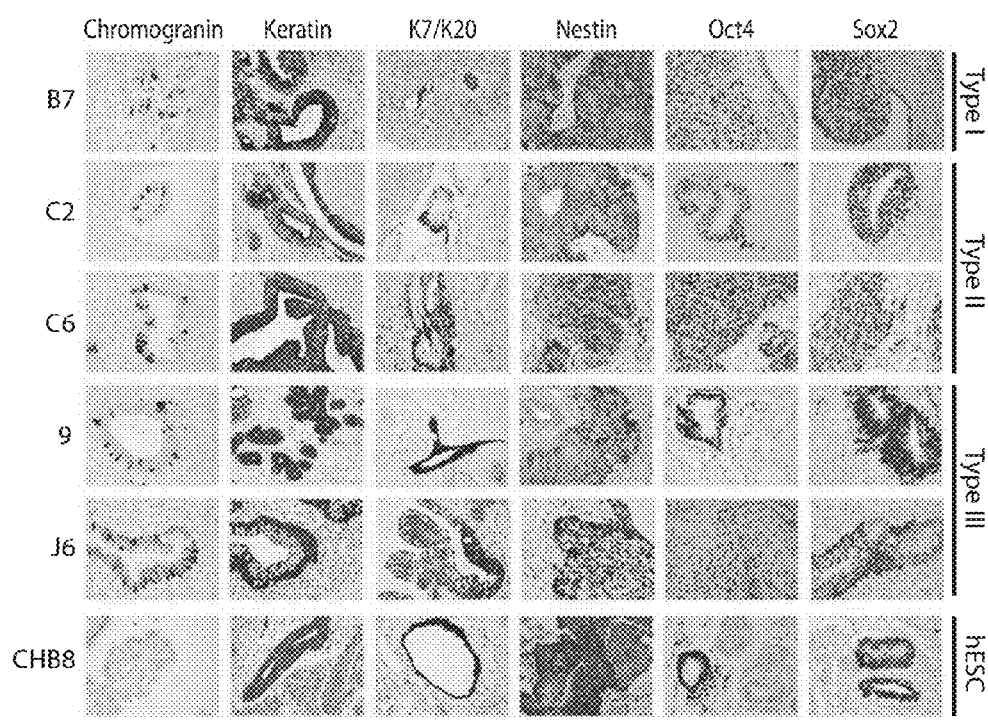
FIG. 10: Immunohistochemistry of various tissue/lineage specific and pluripotency markers on teratomas derived from types I, II, III, and human embryonic stem cell lines. (a) Chromogranin, a marker of neuroendocrine cells (neuroectoderm lineage), stained positive in all lines studied except for the human ES cell line CHB8. (b) Structures staining positive for Keratin, a marker representing the differentiation potential of all three germ layers, were found to be present in all cell lines studied. (c) Structures positive for K7, a marker representing either endodermal or mesodermal differentiation, were found to be present in all cell lines studied whereas structures positive for K20, a marker representing definitive endoderm, were only present in the iPS cell line J6. (d) Nestin, a marker representing neuroectoderm, was present in all cell lines studied. All cell lines studied have some percentage of positivity for the pluripotency markers OCT4 (e) and SOX2 (f).

To determine if these results extend to reprogramming of postnatal fibroblasts FACS and live immunostaining using BJ1 and ADA fibroblasts was performed. Emergence of the three main colony types I-III was confirmed (data not shown), as was the order of marker changes (FIG. 10a-b). Again, there were more TRA-1-60$^+$ cell clusters early during reprogramming (~day 13-16) than there were type III colonies at day 30-35, and type III colonies were outnumbered by (mostly Alkaline Phosphatase-positive) non-type III colonies (data not shown). Many non-type III colonies were small, deteriorating, or had grown into diffuse or piled-up colonies. Several instances of aberrant "type X" colonies (TRA-1-60$^+$SSEA-4$^{low/-}$GFP$^+$Hoechst$^{bright}$; data not shown) were observed, but these colonies could not be expanded in hES cell media. Nevertheless, expandable type I-III lines were established, and all lines included colonies that morphologically resemble hES cell colonies (FIG. 7b). Gene expression and genomic DNA methylation analyses confirmed that type I and II colonies are incompletely reprogrammed, and REX1, DNMT3B and ABCG2 were validated as markers that distinguish type III and hES/hiPS from type I and II cell cultures (FIG. 8).

Figure 9:
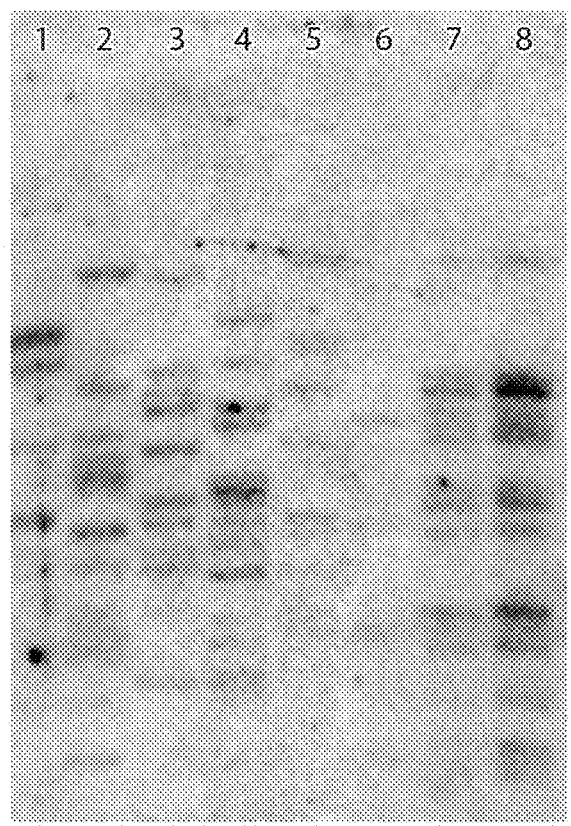
FIG. 9: Southern blot analysis of viral sequences Genomic Southern blot analysis using a probe that detects proviral sequences confirms that the type III culture is indeed a derivative of the parental type II culture. Note the identical banding pattern between these two lines (lanes 7 and 8), and the diverse banding pattern observed with unrelated human iPS cell lines (lanes 1-6).

During expansion of type II cell lines conversion to a more fully reprogrammed state (type III) was observed. This conversion, or completion of reprogramming, occurred spontaneously (in ~25% of dH1f-derived type II lines). Conversion typically began in a small minority of colonies (data not shown). A pure type III line was derived by several rounds of mechanical picking, and Southern blot analysis confirmed that it was indeed the product of a true conversion event and not a cross-contamination (FIG. 9).

When reprogramming was performed in chemically defined media (mTeSR) on Matrigel instead of KOSR media on feeders, enrichment of type III colonies relative to non-type III colonies was observed, indicating that culture conditions can favorably promote reprogramming outcomes. This phenomenon was observed in one primary fibroblast line (ADA; data not shown) as well as four ES-derived fibroblast lines (dH1f, dHUES2f, dCHB3f, dCHB5f).

To test their in vivo differentiation potential, type I, II and III cells were injected into immunodeficient mice. Type III and most type II cells formed tumors that were identified as teratomas with differentiation into multiple germ-layers, whereas type I cells formed poorly differentiated tumors reminiscent of embryonal carcinomas, or no tumors at all (data not shown). The degree of differentiation correlated with that of reprogramming (Table 1 and FIG. 10).

Without wishing to be bound by theory, the data described herein indicate that reprogramming is a highly orchestrated process in which specific molecular events occur in a consistent sequence and within a limited timeframe. While most transduced cells show some phenotypic changes, the vast majority fail to become fully reprogrammed. Once a "milestone" has been missed (e.g., failure to up-regulate TRA-1-60 or SSEA-4, or to silence GFP), cells typically remain fixed in their incompletely reprogrammed state and fail to expand, but occasionally give rise to type I or type II colonies. Repeated microscopic scanning of large areas of immunostained cells in situ allowed identification of emerging iPS cell clusters at an early stage, before they become detectable by FACS (FIG. 7). The approach described herein permits the fate of the same cells to be observed over time.

Time course analyses of mouse and human reprogramming have been studied using doxycycline-inducible systems (Maherali, N., et al. (2008) *Cell Stem Cell* 3, 340-5; Hockemeyer, D., et al. (2008) *Cell Stem Cell* 3, 346-53; Brambrink, T., et al. (2008) *Cell Stein Cell* 2, 151-9; Stadtfeld, M., et al. (2008) *Cell Stem Cell* 2, 230-40). Together with the data described herein, these studies show that the kinetics of human reprogramming, though somewhat variable in different cell types, is similar to that of mouse cells. The first step, extinction of the differentiation marker CD13, is detected as early as day 2, comparable to the down-regulation of Thy-1 in mouse embryonic fibroblasts. Up-regulation of SSEA-4 is detected on day 2 to 6 followed by TRA-1-60 and NANOG as early as day 6 to 13. However, in a human cell system, first detection of nuclear NANOG (observed around day 6-10) does not mark the fully reprogrammed state, as TRA-1-60$^+$NANOG$^+$ positive cell clusters often fail to give rise to human iPS cell colonies and some type II colonies are NANOG$^+$.

Due to the lack of selectable markers that have proven so valuable in studies of mouse cell reprogramming, human iPS cells have been isolated in previous studies based on the distinct morphology of human ES cell colonies (Park, I. H., et al. (2008) *Nature* 451, 141-6; Takahashi, K., et al. (2007) *Cell* 131, 861-72; Yu, J., et al. (2007) *Science* 318, 1917-20). In one study, live TRA-1-81 staining was used to distinguish fully reprogrammed iPS cell colonies at day 21-28 from other types of colonies (Lowry, W. E., et al. (2008) *Proc Natl Acad Sci USA* 105, 2883-8). More recently it was reported that TRA-1-60/SSEA-4 double positive staining represents reprogrammed iPS cells at day 6-8 (Hockemeyer, D., et al. (2008) *Cell Stem Cell* 3, 346-53). The present study shows that in addition to TRA-1-60/SSEA-4 double positive staining, colony size or cellularity (as an indicator of proliferative capacity/absence of senescence) along with a Hoechst$^{dim}$ phenotype is required to accurately predict reprogramming success. The majority of early TRA-1-60$^+$SSEA-4$^+$ cells are not on a trajectory to reach a fully reprogrammed state, but instead senesce, die, or remain partially reprogrammed. The data described herein highlight a significant promiscuity of expression of pluripotency markers during reprogramming, and indicate that no single marker is adequate to indicate the fully reprogrammed state. Retroviral gene silencing, which can be detected as early as day 4, is one of the most specific single markers of reprogramming success, but cannot readily be assessed with non-integrating reprogramming strategies (Okita, K., et al. (2008) *Science* 322, 949-53; Yu, J., et al. (2009) *Science*). However, as shown herein, the Hoechst$^{dim}$ phenotype of emerging iPS cell colonies can be used reliably as a live cell surrogate marker for silencing.

The lack of a single definitive assay for pluripotency of human cells continues to pose a challenge to the iPS cell field (Maherali, N. & Hochedlinger, K. (2008) *Cell Stem Cell* 3, 595-605; Daley, G. Q., et al. (2009) *Cell Stem Cell* 4, 200-1; Ellis, J., et al. (2009) *Cell Stem Cell* 4, 198-9). Incompletely reprogrammed colonies can exhibit some features of reprogramming, including down-regulation of fibroblast markers, up-regulation of pluripotency markers, changes in the histone modification state, acquisition of ES cell-like morphological appearance, and ability to form teratoma-like tumors. SSEA-4, Alkaline Phosphatase, hTERT, or GDF-3, fail to reliably distinguish partially reprogrammed from bona fide iPS cell lines. Described herein are derivation conditions in which fully reprogrammed colonies predominate over incompletely reprogrammed colonies.

generating either embryonal carcinoma (EC)-like tumors or teratomas (T) are shown in column 4. Percent positively identified by immunohistochemistry of markers OCT4, SOX2, Keratin and Nestin are shown in columns 5-8. All lines studied showed structures representing both the mesoderm and ectoderm lineages as shown in columns 9 and 10. The presence of endodermal-derived structures varied amongst the cell lines studied and were scored as follows: a score of '−' indicates that there are no epithelial structures suggestive of endodermal differentiation present; however, complete lack of endodermal differentiation cannot be entirely excluded; "*" indicates that epithelial structures are present that have the potential to differentiate into all three germ layers including endoderm though definitive evidence suggesting the presence or absence of endodermal derivation is lacking; '+' represents definitive identification of endodermal differentiation. The histopathological and immu-

TABLE 1

Quantification of the differentiation potential in teratomas derived from types I, II, III, and human embryonic stem cell lines.

| Cell line | Type | H&E (%) Differentiated | Tumor Type | OCT4 % | SOX2 % | Keratin % | Nestin % | Mesod. | Ectod. | Endod. |
|---|---|---|---|---|---|---|---|---|---|---|
| B7 | I | 5 | EC | >80 | 90 | 5 | 50 | + | + | − |
| G2 | II | <5 | EC | N/A | N/A | N/A | N/A | + | + | − |
| S + T | II | 5 | EC | 50-75 | 50 | 5 | 30 | + | + | − |
| C6 | II | 45 | T | 50 | 50 | 25 | 40 | + | + | * |
| C2 | II | 80 | T | <5 | 20 | 20 | 80 | + | + | * |
| 9 | III | 70 | T | <1 | 50 | 30 | 50 | + | + | * |
| J6 | III | 95 | T | <1 | <10 | 20 | 10 | + | + | + |
| 1C-3 | III | 90 | T | <1 | 30 | 25 | 40 | + | + | + |
| CHB10 | hESC | 90 | T | 0 | <10 | 25 | 5 | + | + | + |

Approximate percent differentiation was quantified using whole section H&E stains as shown in column 3. Cell lines nohistochemical evaluation of teratomas was blinded to the type of iPS cell (I, II, III) that was analyzed.

TABLE 2

Details on cell line sources and characteristics, media, and culture methods. Standard human ES media contains DMEM/F12, 20% KOSR, 10 ng/mL of human recombinant basic fibroblast growth factor, 1x non-essential amino acid, 0.1 mM (β-ME, 1 mM L-glutamine, 50 units/mL penicillin and 50 ug/mL streptomycin. Fibroblast media contains α-MEM, 10% inactivated fetal serum, 50 units/mL penicillin and 50 ug/mL streptomycin. MEFs: CF1 mouse embryonic fibroblasts (Global Stem). Matrigel and chemically defined mTeSR medium (Stem Cell Technologies).
Details on cell line sources and characteristics, media, and culture methods

| Cell Line | Additional Description | Sources/References | Media/Coating |
|---|---|---|---|
| H1-OGN | H1.1 hES cells with GFP and neo integrated into the OCT4 locus | Zwaka, T. P. 2003. | Human ES medium; MEFs |
| BGO1 | Human ES cell line | BresaGen Inc. | Human ES medium; MEFs |
| Type I | Reprogramming intermediate (GFP+ SSEA-4+ TRA-1-60+) | This publication | Human ES medium; MEFs |
| Type II | Reprogramming intermediate (GFP+ SSEA-4+ TRA-1-60+) | This publication | Human ES medium; MEFs |
| Type III (iPS) | Fully reprogrammed iPS cells (GFP+ SSEA-4+ TRA-1-60+) | This publication | Human ES medium; MEFs |
| Matrigel-iPS | Fully reprogrammed iPS cells derived on Matrigel | This publication | mTeSR medium, Matrigel |
| dH1f | Fibroblast lines differentiated from the human ES cell lines H1-OGN | Park, I. H. et. al. 2008. | Fibroblast medium |
| dCHB3f | Fibroblast lines differentiated from the human ES cell line CHB3 | HSCI/CHB hESC Core | Fibroblast medium |
| dCHB5f | Fibroblast lines differentiated from the human ES cell line GHB5 | HSCI/CHB hESC Core | Fibroblast medium |
| dHues2f | Fibroblast lines differentiated from the human ES cell line Hues 2 | Hues Cell Facility | Fibroblast medium |
| Detroit-551 | Primary fetal skin fibroblast | ATCC | Fibroblast medium |
| BJ1 | Primary neonatal foreskin fibroblast | ATCC | Fibroblast medium |
| ADA | Primary postnatal fibroblast from ADA-SCID patient | Coriell | Fibroblast medium |

TABLE 3

Protocol for immunohistochemistry for samples

| Antibody | Company | Catalog# | Species | Clone | Ag Retrieval | Primary Dilution | Secondary | Stain System | Control Tissue | Cellular stain |
|---|---|---|---|---|---|---|---|---|---|---|
| Chromogranin | Chemicon | MAB5268 | Mouse | LK2H10 (2) | citrate PC | 6000 | polymer-M | Envision | S/M/A | cytoplasmic |
| CK7 | Dako | M7018 | Mouse | OV-TL 12/30 | 10' Protease | 1000 | polymer-M | Envision | Breast | cytoplasmic |
| CK20 | Dako | M7019 | Mouse | Ks20.8 | 10' Protease | 50 | polymer-M | Envision | S/M/A | cytoplasmic |
| NANOG | R&D system | AF1997 | Goat | | citrate PC | 1000 | rabbit goat | ABC | Nanog++ | nuclear |
| Nestin | Chemicon | AB5922 | Rabbit-poly | | none | 6000 | polymer-R | Envision | GIST | cytoplasmic |
| SOX-2 | Chemicon | AB5603 | Rabbit-poly | | citrate PC | 1500 | polymer-R | Envision | | |
| OCT-4. | Abcam | ab19857 | Rabbit-poly | | citrate PC | 500 | polymer-R | Envision | | |

TABLE 4

Primer sets in the characterization of cell lines

| Gene | Forward sequence | Reverse sequence |
|---|---|---|
| B-ACTIN | TGAAGTGTGACGTGGACATC | GGAGGAGCAATGATCTTGAT |
| NANOG | TGAACCTCAGCTACAAACAG | TGGTGGTAGGAAGAGTAAAG |
| hTERT | TGTGCACCAACATCTACAAG | GCGTTCTTGGCTTTCAGGAT |
| REX1 | TCGCTGAGCTGAAACAAATG | CCCTTCTTGAAGGTTTACAC |
| GDF3 | AAATGTTTGTGTTGCGGTCA | TCTGGCACAGGTGTCTTCAG |
| OCT4 Endo | CCTCACTTCACTGCACTGTA | CAGGTTTTCTTTCCCTAGCT |
| OCT4 Total | AGCGAACCAGTATCGAGAAC | TTACAGAACCACACTCGGAC |
| SOX2 Endo | CCCAGCAGACTTCACATGT | CCTCCCATTTCCCTCGTTTT |
| SOX2 Total | AGCTACAGCATGATGCAGGA | GGTCATGGAGTTGTACTGCA |
| MYC Endo | TGCCTCAAATTGGACTTTGG | GATTGAAATTCTGTGTAACTGC |
| MYC Total | ACTCTGAGGAGGAACAAGAA | TGGAGACGTGGCACCTCTT |
| KLF4 Endo | GATGAACTGACCAGGCACTA | GTGGGTCATATCCACTGTCT |
| KLF4 Total | TCTCAAGGCACACCTGCGAA | TAGTGCCTGGTCAGTTCATC |
| ABCG2 | TACCTGTAAGTGTACTTCAT | GGTCATGAGAAGTGTTGCTA |
| DNMT3B | ATAAGTCGAAGGTGCGTCGT | GGCAACATCTGAAGCCATTT |
| OCT 4-4 (Bisulfite) | GGATGTTATTAAGATGAAGATAGTTGG | CCTAAACTCCCCTTCAAAATCTATT |
| NANOG3 (Bisulfite) | TTAATTTATTGGGATTATAGGGGTG | AACAACAAAACCTAAAACAAACC |

Forward sequences in Table 4 comprise SEQ ID NOs: 1-17 and the Reverse sequences in Table 4 comprise SEQ ID NOs: 18-34.

TABLE 5

Primer sequences for ChIP analysis

| Primer | Sequence (5'-3') |
|---|---|
| hOCT3/4-ChIP-S2 | TTGCCAGCCATTATCATTCA |
| hOCT3/4-ChIP-AS2 | TATAGAGCTGCTGCGGGATT |
| hSOX2-ChIP-S1 | GAGAAGGGCGTGAGAGAGTG |
| hSOX2-ChIP-AS1 | AAACAGCCAGTGCAGGAGTT |
| hNANOG-ChIP-S2 | GATTTGTGGGCCTGAAGAAA |
| hNANOG-ChIP-AS2 | GGAAAAAGGGGTTTCCAGAG |
| hCDX2-ChIP-S1 | CCCCTAGCTCGCCTCCAGTTATGCACG |
| hCDX2-ChIP-AS1 | CCCAAGGAAATTACTCGCCCTCCGCAC |
| hPAX6-ChIP-S1 | TTGTGTGAGAGCGAGCGGTGCATTTG |
| hPAX6-ChIP-AS1 | CACCGCTCCTCACTGGCCCATTAGC |
| hHAND1-ChIP-S1 | CCATTGGCTCCCGGGAGAGGTTGAC |
| hHAND1-ChIP-AS1 | CCGGGCAAGGCTGAAAATGAGACGC |
| hGATA6-ChIP-S1 | TGAGCGCAGTTCCGACCCACAGCCTG |
| hGATA6-ChIP-AS1 | GGGCGAGCGCGAGTCCGGGGTCTG |
| hZFPM2-ChIP-S1 | TAGGGAGAGACTGAGATTTCTTTGTGCCCC |
| hZFPM2-ChIP-AS1 | CCTTCTGCAGTTGTCACCGCGTCAA |
| ChIP Control S | GAGGTCTCGTATTTGCTGCATCGTA |
| ChIP Control AS | GCTAATTTCCTCTCCACCCCAACCA |

Sequences in Table 5 comprise SEQ ID NOs: 35-52.

Methods

Cell Culture

Details on cell line sources and characteristics, media, and culture methods can be found in Table 2. Expansion of individual clones from both MEF- and Matrigel-derived reprogramming was performed through manual picking of a single colony into a 96 well (appropriately coated). Following two manual passages, cell lines were then enzymatically passaged using Collagenase IV (Invitrogen) for MEF-derived clones and Dispase (Stem Cell Technologies) for Matrigel-derived clones. Karyotype analyses of cell lines were performed by Cell Line Genetics (available on the world wide web at clgenetics.com/). The developmental potential of newly established human iPS cell lines was tested by standard intramuscular teratoma assays performed in immunodeficient mice. The histopathological evaluation of teratomas was performed by a pathologist who was blinded to the type of iPS cell (I, II, III) that they were derived from. A detailed protocol for immunohistochemistry of tumor sections can be found in Table 3.

Retroviral Production and Human iPS Cell Induction for Live Cell Imaging

Retroviral particles that confer expression of OCT4, SOX2, KLF4 and c-MYC were prepared as described previously (Park, I. H., et al. (2008) Nat Protoc 3, 1180-6). $1 \times 10^5$ fibroblasts per 10 cm$^2$ well were exposed to the retroviral particles at an MOI of 2.5 per factor in the presence of protamine sulfate. To capture the live cell imaging, infected cells were trypsinized and $5 \times 10^4$ cell were replated per well of a six well plate pre-plated with $5.5 \times 10^4$ irradiated CF1 MEFs six days after infection in fibroblast medium. Human ES cell culture medium was changed daily starting on day 7. At the end of the time course, some wells were fixed with 4% paraformaldehyde for intracellular immunostaining. For time courses starting earlier than day 7, $5 \times 10^4$ cells were plated one day prior to infection onto a well of a six-well plate. On day 6 post-infection, $5.5 \times 10^4$ CF1 MEFs were plated on top of the infected fibroblasts, and at day 7, medium was changed to human ES cell culture medium and subsequently fed daily. For Matrigel studies, $5 \times 10^4$ infected fibroblasts were split onto a Matrigel-coated well at day 7 post-infection and medium was changed to chemically defined mTeSR medium and fed daily.

Flow Cytometry

During the first seven days of the reprogramming process, infected fibroblasts were harvested using 0.25% trypsin/EDTA. On and after day 8 of the reprogramming process, cells were collected by a cell scraper after treating with 1 mg/mL Collagenase IV for 5 minutes at 37° C. and the pellet was treated with 1× Accutase (Chemicon) for 5 minutes at 37° C. Cells were strained using a 40 micron nylon cell strainer and resuspended in FACS buffer, containing Phosphate Buffered Saline (PBS; Invitrogen) and 1% Bovine Serum Albumin (BSA; GIBCO). FACS analysis was performed on a BD FACSCalibur or a BD LSRII using the following antibodies: CD13-PE, CD13-APC (1:100; Biolegend), SSEA-4-Alexa Fluor 647, TRA-1-60-PE, TRA-1-60-Alexa Fluor 647 (1:100; BD Biosciences).

Immunostaining

Cells were washed with PBS and fixed in 4% paraformaldehyde for 20 minutes at room temperature. After 3×PBS washes, cells were blocked in 3% BSA (GIBCO) and 5% donkey serum (Sigma) for 30 minutes at room temperature. If nuclear permeation was needed, cells were treated with 0.2% TritonX (Sigma) in PBS for 30 minutes followed by 3×PBS washes prior to blocking. Cells were then stained with primary or conjugated antibodies at 4° C. overnight. After 3×PBS washes, cells were stained with secondary antibodies for 3 hours in the dark at 4° C. Cells were then incubated for 10 minutes in 5 µg/ml DAPI (Invitrogen) or 1 µg/mL Hoechst 33342 (Invitrogen), followed by 3×PBS washes prior to visualization. The following antibodies were used: TRA-1-60-Alexa Fluor 647, SSEA-4-Alexa Fluor 555 (1:100; BD Biosciences), D7FIB-RPE (1:15; Serotec) and CD13-PE (1:100; Biolegend). Cells stained with NANOG (Abcam) were fixed using 90% methanol (−20° C.) for 5 minutes, followed by 3×PBS washes prior to blocking. Cells were blocked and permeated using 0.1% Saponin (Sigma) and 1% donkey serum in PBS for 2 hours at room temperature. Primary antibody was used at a 1:1000 dilution in 1% donkey serum and secondary anti-rabbit IgG Alexa Fluor 555 (Invitrogen) was used at a 1:2000 dilution.

Live Cell Imaging and Image Analysis

For live imaging, wells were stained by addition of TRA-1-60-Alexa Fluor 647 and SSEA-4-Alexa Fluor 555, or CD13-PE (1:100). After 1.5 hours, Hoechst (Invitrogen) was added (0.5 µg/ml final) and cells were stained for an additional 30 minutes. Wells were washed 3 times with DMEM/F12 base media lacking phenol red and imaged in standard human ES cell culture medium lacking phenol red. Images were acquired using a BD Pathway 435 imager equipped with a 10× (hES-derived fibroblasts) or 4× (postnatal fibroblasts) objective. Every 2-4 days, areas corresponding to 4 to 40 cm$^2$ were imaged. Four images were acquired per frame (Hoechst, GFP, Alexa Fluor 555/PE, Alexa Fluor 647). GFP acquisition settings were optimized for detection of high-level proviral GFP expression. Post-acquisition image processing was performed using ImageJ (flatfield-correction, background subtraction, intensity- and area measurements; available on the world wide web at rsb.info.nih.gov/ij/) and Adobe Photoshop (pseudocoloring, multi-color composites).

Quantitative Real Time PCR

Direct application of TRIZOL (Invitrogen) onto adherent cells was performed for RNA isolation. RNA clean up was performed using QIAGEN RNeasy Kit. First strand cDNA synthesis was performed using SuperScript III Reverse Transcriptase Kit (Invitrogen). RT-PCR was performed with primer sets corresponding to Table 4. Quantitative PCR analyses were performed using the Stratagene Mx3005p instrument and Brilliant SYBR green master mix.

Bisulfite Genomic Sequencing

Bisulfite treatment of gDNA was carried out using a CpGenome DNA Modification Kit (Chemicon) according to the manufacturer's protocol. Sample treatment and processing were performed simultaneously for all cell lines. Converted gDNA was amplified by PCR using primers within the OCT4 and NANOG promoters (see Table 4 for sequences). PCR products were cloned into bacteria using TOPO TA cloning (Invitrogen).

ChIP Assay

ChIP assays were performed as described previously (Feng, B., et al. (2009) Nat Cell Biol 11, 197-203) using anti-H3K4me3 (Abcam) and anti-H3K27me3 (Upstate) antibodies. Quantitative PCR analyses were performed as described above. Threshold cycles (Ct) were determined for both immunoprecipitated DNA and known amounts of DNA. Relative occupancy values (also known as fold enrichments) were calculated by determining the TP efficiency (ratios of the amount of immunoprecipitated DNA to that of the input sample) and normalized to the level observed at a control region, which was defined as 1.0. The coordinates for the control region for the ChIP is chr12:7, 839,777-7,839,966 (hg18 genome build). ChIP primers are listed in Table 5.

Clonal Integration Analysis by Southern Blot gDNA was isolated using DNeasy kit (Qiagen) according to the manufacturer's protocol. 5-10 µg of genomic DNA was digested with NcoI and subjected to Southern blot analysis using a GFP probe to provide a viral integration fingerprint.

The invention claimed is:

1. A method for detecting complete somatic cell reprogramming in a culture, the method comprising:
   (a) contacting a somatic cell induced to reprogram, or its progeny, with a plurality of detectably labeled binding moieties that bind Rex1, DNMT3B, and ABCG2; and
   (b) detecting the binding of one or more moieties to the cell, or its progeny, to Rex1, DNMT3B, and ABCG2 expressed by a cell in the culture;
   wherein binding indicates a fully-reprogrammed cell.

2. The method of claim 1, further comprising detecting a stem cell marker selected from the group consisting of SSEA1, SSEA4, TRA160, CD9, Fbx15, Ecat1, Esg1, Eras, Gdf3, Fgf4, Cripto, Dax1, Zpf296, Slc2a3, Utf1, Oct4, SOX2, Nat1 and/or NANOG.

3. The method of claim 1, further comprising detecting silencing of the expression of a viral reporter gene.

4. The method of claim 1, wherein the somatic cell comprises a fibroblast.

5. The method of claim 4, wherein expression of fibroblast marker CD13 is down-regulated.

6. The method of claim 1, further comprising repeating steps (a)-(b) at a plurality of time points.

7. The method of claim 1, wherein each of the detectably labeled moieties comprises a fluorescent moiety.

8. The method of claim 1, wherein the reprogrammed cell is pluripotent.

9. The method of claim 1, wherein the reprogrammed cell comprises a side population (SP) phenotype.

10. The method of claim 9, wherein the SP phenotype comprises a HOECHST$^{dim}$ phenotype.

11. A method for identifying a fully reprogrammed induced pluripotent stem cell (iPS) cell from a culture of cells, the method comprising:
   (a) contacting a somatic cell induced to reprogram, or its progeny, with a plurality of detectably labeled binding moieties that bind Rex1, DNMT3B, and ABCG2 expressed by a cell in the culture; and
   (b) detecting the binding of one or more of the moieties to the cell, or its progeny, to Rex1, DNMT3B, and ABCG2 expressed by a cell in the culture;
   wherein the presence of Rex1, DNMT3B, and ABCG2 indicates a fully reprogrammed iPS cell.

12. The method of claim 11, further comprising detecting a stem cell marker selected from the group consisting of SSEA1, SSEA4, TRA160, CD9, Fbx15, Ecat1, Esg1, Eras, Gdf3, Fgf4, Cripto, Dax1, Zpf296, Slc2a3, Utf1, Oct4, SOX2, Nat1 and/or NANOG.

13. The method of claim 12, wherein the stem cell markers further comprise TRA160.

14. A method for screening for an agent that promotes complete somatic cell reprogramming in a culture, the method comprising:
   (a) contacting a somatic cell with a plurality of detectably labeled moieties that bind Rex1, DNMT3B, and ABCG2 expressed by a cell in the culture, in the presence and absence of a candidate reprogramming agent; and
   (c) detecting the degree of cell labeling with one or more of the detectably labeled moieties of Rex1, DNMT3B, and/or ABCG2;
   wherein if the level of expression of Rex1, DNMT3B, and ABCG2 in the presence of the agent is higher compared to the level of Rex1, DNMT3B, and ABCG2 in the absence of the agent, the agent enhances complete somatic cell reprogramming.

15. The method of claim 14, further comprising detecting a stem cell marker selected from the group consisting of SSEA1, SSEA4, TRA160, CD9, Fbx15, Ecat1, Esg1, Eras, Gdf3, Fgf4, Cripto, Dax1, Zpf296, Slc2a3, Utf1, Oct4, SOX2, Nat1 and/or NANOG.

16. The method of claim 15, wherein the stem cell markers comprise TRA160.

* * * * *

UNITED STATES PATENT AND TRADEMARK OFFICE
CERTIFICATE OF CORRECTION

PATENT NO. : 9,846,164 B2
APPLICATION NO. : 14/194586
DATED : December 19, 2017
INVENTOR(S) : George Q. Daley et al.

Page 1 of 1

It is certified that error appears in the above-identified patent and that said Letters Patent is hereby corrected as shown below:

In the Specification

At Column 1, Line 22, please replace the paragraph entitled "GOVERNMENT SUPPORT" with the following paragraph:
GOVERNMENT SUPPORT
This invention was made with government support under Grant number OD000256, awarded by The National Institutes of Health. The government has certain rights in the invention.

Signed and Sealed this
Twenty-ninth Day of December, 2020

Andrei Iancu
*Director of the United States Patent and Trademark Office*

SEQUENCE LISTING

<160> NUMBER OF SEQ ID NOS: 52

<210> SEQ ID NO 1
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 1
tgaagtgtga cgtggacatc                                              20

<210> SEQ ID NO 2
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 2
tgaacctcag ctacaaacag                                              20

<210> SEQ ID NO 3
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 3
tgtgcaccaa catctacaag                                              20

<210> SEQ ID NO 4
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 4
tcgctgagct gaaacaaatg                                              20

<210> SEQ ID NO 5
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 5
aaatgtttgt gttgcggtca                                              20

<210> SEQ ID NO 6
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 6
cctcacttca ctgcactgta                                              20

<210> SEQ ID NO 7
<211> LENGTH: 20
<212> TYPE: DNA
<213> ORGANISM: Artificial Sequence -continued

```
<220> FEATURE:
<223> OTHER INFORMATION: synthetic polynucleotide

<400> SEQUENCE: 7
agcgaaccag tatcgagaac                                                 20

<210> SEQ ID NO 8
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 8
cccagcagac ttcacatgt                                                  19

<210> SEQ ID NO 9
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 9
agctacagca tgatgcagga                                                 20

<210> SEQ ID NO 10
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 10
tgcctcaaat tggactttgg                                                 20

<210> SEQ ID NO 11
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 11
actctgagga ggaacaagaa                                                 20

<210> SEQ ID NO 12
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 12
gatgaactga ccaggcacta                                                 20

<210> SEQ ID NO 13
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 13
tgtcaaggca cacctgcgaa                                                 20
```

```
<210> SEQ ID NO 14
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 14
tacctgtata gtgtacttca t                                              21

<210> SEQ ID NO 15
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 15
ataagtcgaa ggtgcgtcgt                                                20

<210> SEQ ID NO 16
<211> LENGTH: 27
<212> TYPE: DNA
<213> ORGANISM: Artificial Sequence
<220> FEATURE:
<223> OTHER INFORMATION: synthetic polynucleotide

<400> SEQUENCE: 16
ggatgttatt aagatgaaga tagttgg                                        27

<210> SEQ ID NO 17
<211> LENGTH: 25
<212> TYPE: DNA
<213> ORGANISM: Artificial Sequence
<220> FEATURE:
<223> OTHER INFORMATION: synthetic polynucleotide

<400> SEQUENCE: 17
ttaatttatt gggattatag gggtg                                          25

<210> SEQ ID NO 18
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 18
ggaggagcaa tgatcttgat                                                20

<210> SEQ ID NO 19
<211> LENGTH: 20
<212> TYPE: DNA
<213> ORGANISM: Artificial Seuqnece
<220> FEATURE:
<223> OTHER INFORMATION: synthetic polynucleotide

<400> SEQUENCE: 19
tggtggtagg aagagtaaag                                                20

<210> SEQ ID NO 20
<211> LENGTH: 20
<212> TYPE: DNA
<213> ORGANISM: Artificial Sequence
<220> FEATURE:
<223> OTHER INFORMATION: synthetic polynucleotide
```

```
<400> SEQUENCE: 20
gcgttcttgg ctttcaggat                                              20

<210> SEQ ID NO 21
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 21
cccttcttga aggtttacac                                              20

<210> SEQ ID NO 22
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 22
tctggcacag gtgtcttcag                                              20

<210> SEQ ID NO 23
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 23
caggttttct ttccctagct                                              20

<210> SEQ ID NO 24
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 24
ttacagaacc acactcggac                                              20

<210> SEQ ID NO 25
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 25
cctcccattt ccctcgtttt                                              20

<210> SEQ ID NO 26
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 26
ggtcatggag ttgtactgca                                              20

<210> SEQ ID NO 27
```

```
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 27
gattgaaatt ctgtgtaact gc                                              22

<210> SEQ ID NO 28
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 28
tggagacgtg gcacctctt                                                  19

<210> SEQ ID NO 29
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 29
gtgggtcata tccactgtct                                                 20

<210> SEQ ID NO 30
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 30
tagtgcctgg tcagttcatc                                                 20

<210> SEQ ID NO 31
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 31
ggtcatgaga agtgttgcta                                                 20

<210> SEQ ID NO 32
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 32
ggcaacatct gaagccattt                                                 20

<210> SEQ ID NO 33
<211> LENGTH: 25
<212> TYPE: DNA
<213> ORGANISM: Artificial Sequence
<220> FEATURE:
<223> OTHER INFORMATION: synthetic polynucleotide

<400> SEQUENCE: 33
```

```
cctaaactcc ccttcaaaat ctatt                                          25

<210> SEQ ID NO 34
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 34
aacaacaaaa cctaaaaaca aacc                                           24

<210> SEQ ID NO 35
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 35
ttgccagcca ttatcattca                                                20

<210> SEQ ID NO 36
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 36
tatagagctg ctgcgggatt                                                20

<210> SEQ ID NO 37
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 37
gagaagggcg tgagagagtg                                                20

<210> SEQ ID NO 38
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 38
aaacagccag tgcaggagtt                                                20

<210> SEQ ID NO 39
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 39
gatttgtggg cctgaagaaa                                                20

<210> SEQ ID NO 40
<211> LENGTH: 20
<212> TYPE: DNA
```

```
<213> ORGANISM: Artificial Sequence
<220> FEATURE:
<223> OTHER INFORMATION: synthetic polynucleotide

<400> SEQUENCE: 40
ggaaaaaggg gtttccagag                                                   20

<210> SEQ ID NO 41
<211> LENGTH: 27
<212> TYPE: DNA
<213> ORGANISM: Artificial Sequence
<220> FEATURE:
<223> OTHER INFORMATION: synthetic polynucleotide

<400> SEQUENCE: 41
cccctagctc gcctccagtt atgcacg                                           27

<210> SEQ ID NO 42
<211> LENGTH: 27
<212> TYPE: DNA
<213> ORGANISM: Artificial Sequence
<220> FEATURE:
<223> OTHER INFORMATION: synthetic polynucleotide

<400> SEQUENCE: 42
cccaaggaaa ttactcgccc tccgcac                                           27

<210> SEQ ID NO 43
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 43
ttgtgtgaga gcgagcggtg catttg                                            26

<210> SEQ ID NO 44
<211> LENGTH: 25
<212> TYPE: DNA
<213> ORGANISM: Artificial Sequence
<220> FEATURE:
<223> OTHER INFORMATION: synthetic polynucleotide

<400> SEQUENCE: 44
caccgctcct cactggccca ttagc                                             25

<210> SEQ ID NO 45
<211> LENGTH: 25
<212> TYPE: DNA
<213> ORGANISM: Artificial Sequence
<220> FEATURE:
<223> OTHER INFORMATION: synthetic polynucleotide

<400> SEQUENCE: 45
ccattggctc ccgggagagg ttgac                                             25

<210> SEQ ID NO 46
<211> LENGTH: 25
<212> TYPE: DNA
<213> ORGANISM: Artificial Sequence
<220> FEATURE:
<223> OTHER INFORMATION: synthetic polynucleotide

<400> SEQUENCE: 46
ccgggcaagg ctgaaaatga gacgc                                             25
```

```
<210> SEQ ID NO 47
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 47
tgagcgcagt tccgacccac agcctg                                              26

<210> SEQ ID NO 48
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 48
gggcgagcgc gagtccgggg tctg                                                24

<210> SEQ ID NO 49
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 49
tagggagaga ctgagatttc tttgtgcccc                                          30

<210> SEQ ID NO 50
<211> LENGTH: 25
<212> TYPE: DNA
<213> ORGANISM: Artificial Sequence
<220> FEATURE:
<223> OTHER INFORMATION: synthetic polynucleotide

<400> SEQUENCE: 50
ccttctgcag ttgtcaccgc gtcaa                                               25

<210> SEQ ID NO 51
<211> LENGTH: 25
<212> TYPE: DNA
<213> ORGANISM: Artificial Sequence
<220> FEATURE:
<223> OTHER INFORMATION: synthetic polynucleotide

<400> SEQUENCE: 51
gaggtctcgt atttgctgca tcgta                                               25

<210> SEQ ID NO 52
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 52
gctaatttcc ttctccaccc caacca                                              26
```